(12) United States Patent
Kron et al.

(10) Patent No.: US 6,245,539 B1
(45) Date of Patent: Jun. 12, 2001

(54) HUMAN ASPARAGINYL-TRNA SYNTHETASE DNA

(75) Inventors: Michael A. Kron, Okemos, MI (US); Michael M. Hartlein, Victor Hugo (FR); Michito Hirikata, Tokyo (JP)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/167,299

(22) Filed: Oct. 6, 1998

(51) Int. Cl.[7] ........................................... C12N 9/00
(52) U.S. Cl. .................. 435/183; 435/320.1; 435/282.3; 435/252.33; 435/419; 435/254.11; 435/325; 536/23.2
(58) Field of Search ................................ 435/183, 320.1; 536/23.2

(56) References Cited

U.S. PATENT DOCUMENTS

| | | |
|---|---|---|
| 5,079,172 | 1/1992 | Hari et al. . |
| 5,561,054 | 10/1996 | Kron et al. . |
| 5,629,188 | 5/1997 | Shiba et al. . |
| 5,663,066 | 9/1997 | Raben et al. . |
| 5,695,962 | 12/1997 | Kron et al. . |
| 5,721,116 | 2/1998 | Kron et al. . |
| 5,726,195 | 3/1998 | Hill et al. . |
| 5,747,315 | 5/1998 | Lawlor . |
| 5,756,327 | 5/1998 | Sassanfar et al. . |
| 5,759,833 | 6/1998 | Shiba et al. . |

FOREIGN PATENT DOCUMENTS

| | | |
|---|---|---|
| WO 88/08534 | 11/1988 | (WO) . |
| WO 91/12528 | 8/1991 | (WO) . |

OTHER PUBLICATIONS

Yu et al. GenBank Accesion No. HSU79254, Dec. 1996.*
Beaulande et al. Nucleic Acids Research (1998) 26(2): 521–524, Jan. 1998.*
Cusak et al. Sequence, structural and evolutionary relationships between class 2 aminoacyl–tRNA synthetases. Nucleic Acids Research (1991) 19(13): 3489–3498.*
Eriani, G., et al., Nature 347: 203–206 (1990).
Cusack, S., et al., Nature 347:249–255 (1990).
Anselme, J., et al., Gene 84:481–485 (1989).
Mathews, M. B., et al., Nature 304:177–179 (1983).
Bunn, C. C., et al., J. Exp. Med. 163:1281–1291 (1986).

* cited by examiner

Primary Examiner—Ponnathapu Achutamurthy
Assistant Examiner—Kathleen Kerr
(74) Attorney, Agent, or Firm—Ian C. McLeod

(57) ABSTRACT

The CDNA sequence of human cytosolic asparaginyl-tRNA synthesis AsnRS, the bacterial expression of the recombinant enzyme and its activity assays with different sources of tRNA is described. The reactivity with a human autoimmune serum is described. The implication of the human cytoplasmic AsnRS in an autoimmune disorder is a property of this enzyme.

12 Claims, 9 Drawing Sheets

Human

| I | II | III |
|---|---|---|
| Eukaryote extension | Beta Barrel | Carboxy terminus |

```
                        N-terminal extension
             ┌─────────────────────────────────────────────────────────────────────────────────┐
hsASNRS      │MVLAELYVSD REGSDA.TGD GTKEKPFKTG LKALMTVGKE PFPT...IYV DSQKENER.W NVISKSQLKN IKKMWHREQM│  75
bmASNRS      │.MTVYIC. PETGDD.GND GSELKPLRTL YQAMI.ITKS SKGD...FLI RTKKDGKQIW EAASKTALKK SWKHYEQEML│  71
scASNRS      │MSSLYIKE ATGVDELTTA GSQDHPFKTP AYALFASQQK SDATEPKLFV FKTEDNE..Y QEISASALKK ARK..GCDGL│  74
ttASNRS      │                                                                                 │
             └─────────────────────────────────────────────────────────────────────────────────┘

┌─────────────────────────────────────────────────────────────────────────────────┐
hsASNRS      │KSESR.....  EKKEAEDSLR REKNLEEAKK ITI│KNDPSLP EPKCVKIGAL EGYRGQRVKV FGWVHRLRRQ GKNLMFLVLR  150
bmASNRS      │KNEKVAAKML EKDATEVGVK ..AALEEAKK ITI│VQIELDTSLS YITGVKIRDL VKHRNERVCI KGWIHRMRRQ GKSLMFFILR  149
scASNRS      │KKKAVKQKEQ SLKKQQKEAE NAAKQLSALN ITI│KEDESLP AAIKTRIYDS YSKVGQRVKV SGWIHRLRS.  NKKVIFVVLR  153
ttASNRS      │                                    .MRVFIDEI ARHVDQEVEL RGWLYQRR.S KGKIHFLILR│  37
             └─────────────────────────────────────────────────────────────────────────────────┘
                                                    β-barrel domain hsASNRS      DGTGYLQCVL ADELCQCY..  .NGVLLSTES SVAVYGMLNL TPKGKQAPGG HELSCDFWEL IGLAPAG..G ADNLINEESD  225
bmASNRS      DGTGFLQVLL MDKLCQTY..  .DALTVNTEC TVEIYGAIKE VPEGKEAPNG HELIADFWKI IGNAPPG..G IDNVLNEEAS  224
scASNRS      DGSGFIQCVL SGDLALAQ..  .QTLDLTLES TVTLYGTIVK LPEGKTAPGG VELNVDYYEV VGLAPGGEDS FTNKIAEGSD  230
ttASNRS      DGTGFLQATV VQGEVPEAVF READHLPQET ALRVWG...R VREDRRAPGG FELAVRDLQV VSR..PQ..G EYPIGPKEHG  110

Motif 1 ######
hsASNRS      VDVQLNNRHM MIRGENMSKI LKARSMVTRC FRDHFFDRGY YEVTPPTLVQ TQVEGGATLF KL........  287
bmASNRS      VDKMLDNRHL VIRGENAAAL LRLRAAATRA MREHFYNAGY LEVAPPTLVQ TQVEGGSTLF NL........  286
scASNRS      PSLLLDQRHL ALRGDALSAV MKVRAALLKS VRRVYDEEHL TEVTPPCMVQ TQVEGGSTLF KM........  292
ttASNRS      IDFLMDHRHL WLRHRRPFAV MRIRDELERA IHEFFGERGF LRFDAPILTP SAVEGTTELF EVELFD....  176
```

FIG. 1A

```
hsASNRS  ..DYFGEEAF LTQSSQLYLE TCLPALGDVF CIAQSYRAEQ SRTRRHLAEY THVEAECPFL TFDDLLNRLE DLVCDVVDRI  365
bmASNRS  ..DYFGEQSF LTQSSQLYLE TCIPTLGDVF HLHCSYRAEK SRTRRHLAEY AHVEAECPFI TLDDLMEKIE ELVCDTVDRL  364
scASNRS  .NYYGEEAY LTQSSQLYLE TCLASLGDVY TIQESFRAEK SHTRRHLSEY THIEAELAFL TFDDLLQHIE TLIVKSVQYV   370
ttASNRS  .....GEKAY LSQSGQLYAE AGALAFAKVY TFGPTFRAER SKTRRHLLEF WMVEPEVAFM THEENMALQE ELVSFLVARV  251

######### Motif 2 ##################
hsASNRS  L.KSP...... .AGSIVHELN PNFQP.PKRP FKRMNYSDAI VWLKEHDVKK EDGTFYEFGE DIPEAPERLM TDT.INEPIL  436
bmASNRS  LADEE...... .AKKLLEHIN PKFQP.PERP FLRMEYKDAI KWLQEHNVEN EFGNTFTYGE DIAEAAERFM TDT.INKPIL  436
scASNRS  LEDPI...... .AGPLVKQLN PNFKA.PKAP FMRLQYKDAI TWLNEHDIKN EEGEDFKFGD DIAEAAERKM TDT.IGVPIF  442
ttASNRS  LERRSREL.. ..EMLGRDPK A.LEPAAEGH YPRLTYKEAV ALVNRIAQED PEVPPLPYGE DFGAPHEAAL S.RRFDRPVF   325 hsASNRS  LCRFPVEIKS FYMQRCPEDS RLTESVDVLM P.NVGEIVGG SMRIFDSEEI LAGYKREGID PTPYYWYTDQ RKYGTCPHGG  515
bmASNRS  LNRFPSEIKA FYMQRDAQDN TLTESVDLLM P.GVGEIVGG SMRIWKFDEL SKAFKNVEID PKPYYWYLDQ RLYGTCPHGG  515
scASNRS  LTRFPVEIKS FYMKRCSDDP RVTESVDVLM P.NVGEITGG SMRIDDMDEL MAGFKREGID TDAYYWFIDQ RKYGTCPHGG  521
ttASNRS  VERYPARIKA FYMEPDPEDP ELVLNDDLLR PEGYGEIIGG SQRIHDLELL RRKIQEFGLP EEVYDWYLDL RRFGSVPHSG  405

##### Motif 3 ############
hsASNRS  YGLGLERFLT WILNRYHIRD VCLYPRFVQR CTP..  546
bmASNRS  YGLGLERFIC WLTNTNHIRD VCLYPRFVGR CVP..  546
scASNRS  YGIGTERILA WLCDRFTVRD CSLYPRFSGR CKP..  552
ttASNRS  FGLGLERTVA WICGLAHVRE AIPFPRMYTR MRP..  436
```

FIG. 1B

HUMAN ASPARAGINYL-TRNA SYNTHETASE DNA

GOVERNMENT RIGHTS

This invention was produced under a grant by the National Institute of Health Grant No. R29A137668. The United States Government has certain rights to this invention. Further, this invention was produced under a grant from the Ministry of Health and Welfare and the Ministry of Education Grant Nos. 07770340 and 08670534.

CROSS-REFERENCE TO RELATED APPLICATION

None

BACKGROUND OF THE INVENTION (1) Field of the Invention

The present invention relates to isolated and sequenced DNA encoding asparaginyl-tRNA synthetase. Further, the present invention relates to test kits and methods for detecting autoimmune diseases which are related to asparaginyl-tRNA synthetase (AsnRS).

(2) Description of Related Art

Aminoacyl-tRNA synthetases (aaRS) are enzymes involved in protein biosynthesis catalyzing the specific attachment of amino acids to their cognate tRNAs. Two classes of synthetases have been defined, each of 10 members, based on their primary and tertiary structures (Eriani, G., et al., Nature 347:203–206 (1990); and Cusack, S., et al., Nature 347:249–255 (1990)). Class II enzymes have three consensus sequence motifs; motif 1 contributes to the dimer interface, whereas motifs 2 and 3 are constituents of the catalytic site. Sub-classification can be made of the class II enzymes based on more extensive sequence and structural similarities (Cusack, S., et al., Nucleic Acids Res. 19:3489–3498 (1991)). In higher eukaryotes, nine aaRS of different specificities (not including AsnRS) are associated within a multi-enzyme complex (Mirande, M., et al., Eur. J. Biochem. 147:281–289 (1985)).

Asparaginyl-tRNA synthetase (AsnRS) is classified as a sub-class IIb enzyme together with the aspartyl- and lysyl-enzymes on the basis of similarities in their N-terminal extensions and the catalytic domains (Cusack, S., et al., Nucleic Acids Res. 19:3489–3498 (1991); Anselme, J., et al., Gene 84:481–485 (1989); Gatti, D. L., et al., J. Mol. Biol. 218:557–568 (1991); and Eriani, G., et al., Nucleic Acids Res., 18:7109–7118 (1990)). The three-dimensional structure of an AsnRS of *Thermus thermophilus* (Seignovett, I., et al., Eur. J. Biochem. 239:501–508 (1996)) further illustrates the strong structural homology between the three class IIb synthetases.

Illustrative of the patent art relating to amino acid synthetases are the following patents: U.S. Patent No. 5,561,054 to Kron et al; U.S. Pat. No. 5,629,188 to Shiba et al; U.S. Pat. No. 5,663,066 to Raben et al; U.S. Pat. No. 5,695,962 to Kron et al; U.S. Pat. No. 5,721,116 to Kron et al; U.S. Pat. No. 5,726,195 to Hill et al; U.S. Pat. No. 5,747,315 to Lawlor; U.S. Pat. No. 5,756,327 to Sassanfar et al; and U.S. Pat. No. 5,759,833 to Shiba et al.

Autoantibodies are found in many patients with polymyositis or dermatomyositis. Some of these patients have antibodies raised against aaRS, of which anti-Jo-1, directed at histidyl-tRNA synthetase (HisRS) is by far the most common (Targoff, I. N., J. Invest. Dermatol., 100:116S–123S (1993)).

Autoantibodies directed against aminoacyl-tRNA synthetases can be found in approximately 25–35% of patients with the chronic, inflammatory muscle disorders, polymyositis (PM) and dermatomyositis (DM) (Targoff, I. N., Rheum. Dis. Clin. North. Am. 20:857–880 (1994)). Each member of this family of enzymes catalyzes the formation of an aminoacyl-tRNA from a specific amino acid and its cognate tRNAs. Autoantibodies to five of these synthetases (histidyl-, threonyl-, alanyl-, isoleucyl-, and glycyl-tRNA synthetases) have been identified in patients with PM and DM (Targoff, I. N., Rheum. Dis. Clin. North. Am 20:857–880 (1994); Mathews, M. B., et al., Nature 304:177–179 (1983); Mathews, M. B., et al., J. Exp. Med. 160:420–434 (1984); Bunn, C. C., et al., J. Exp. Med. 163:1281–1291 (1986); Targoff, I. N., J. Immunol. 144:1737–1743 (1990)). Among these "anti-synthetase antibodies", anti-histidyl tRNA synthetase (anti-Jo-1) is the most common, found in 20–30% of such patients (Targoff, I. N., et al., J. Immunol. 138:2874–2882 (1987); Oddis, C. V., et al., Arthritis Rheum. 33:1640–1645 (1990); Love, L. A., et al., Medicine (Baltimore) 70:360–374 (1991); Hirakata, M., et al., Arthritis Rheum. 35:449–456 (1992); and Marguerie, D., et al., Q. J. Med. 77:1019–1038 (1990)). Anti-threonyl tRNA synthetase (anti-PL-7) and anti-alanyl tRNA synthetase (anti-PL-12) antibodies are less common, found in 3 to 4% of all patients with PM/DM (Mathews, M. B., et al., J. Exp. Med. 160:420–434 (1984); Bunn, C. C., et al., J. Exp. Med. 163:1281–1291 (1986); Marguerie, C., et al., Q. J. Med. 77:1019–1038 (1990); Targoff, I. N., et al., Arthritis Rheum. 31:515–524 (1988); Targoff, I. N., et al., Am. J. Med. 88:241–251 (1990)), while autoantibodies to isoleucyl-tRNA synthetase (anti-OJ) and glycyl-tRNA synthetase (anti-EJ) are the least common, occurring in <2% (Targoff, I. N., J. Immunol. 144:1737–1743 (1990); Targoff, I. N., et al., J. Clin. Invest. 91:2556–2564 (1993); and Targoff, I. N., et al., Arthritis Rheum. 35:821–830 (1992)). Isoleucyl-tRNA synthetase is the only one of these synthetase autoantigens that is a component of the multi-enzyme synthetase complex, and some anti-OJ sera also react with other components of the synthetase complex, but such additional reactivity does not change the immunoprecipitation picture of anti-OJ. Thus, excluding the 9 synthetase activities that are part of the complex, and the 4 other described anti-synthetases, 7 aminoacyl-tRNA syntheses exist for which autoantibodies have not been described, as determined by immunoprecipitation of tRNA. The reason for this selectivity for certain synthetases is not known. With the exception mentioned for anti-OJ, it is extremely rare for a patient to have more than one anti-synthetase (Gelpi, C., et al., Arthritis Rheum. 39:692–697 (1996)).

Anti-Jo-1 and other anti-synthetases have each been associated with a similar syndrome marked by myositis with a high frequency of interstitial lung disease (ILD) (50–80%) and arthritis (50–90%) (Oddis, C. V., et al., Arthritis Rheum. 33:1640–1645 (1990); Love, L A., et al., Medicine (Baltimore) 70:360–374 (1991); Hirakata, M., et al., Arthritis Rheum. 35:449–456 (1992); Marguerie, C., et al., Q. J. Med. 77:1019–1038 (1990); Yoshida, S., et al., Arthritis Rheum. 26:604–611 (1983); and Bernstein, R. M., et al., Br. Med. J. 289:151–152 (1984)), as well as an increase when compared to the overall myositis population in Raynaud's phenomenon (60%), fever with exacerbations (80%), and the skin lesion of the fingers referred to as mechanic's hands (70%) (Love, L. A., et al., Medicine (Baltimore) 70:360–374 (1991)). Other associations, such as an increase in sicca and sclerodactyly have been observed by some investigators (Marguerie, C., et al., Q. J. Med. 77:1019–1038 (1990)).

Although the similarities between patients with different anti-synthetases are most striking, certain differences have been observed, which must be considered preliminary due to the small number of patients with non-Jo-1 anti-synthetases reported. One important difference is that patients with anti-PL-12 are more likely than anti-Jo-1 patients to have ILD and/or arthritis either without myositis or with subclinical signs of muscle disease. Absence of significant myositis over the full course of patients with anti-Jo-1 is rare (<5%), although it may occur. Clinically significant myositis was seen in 60% of U.S. patients with anti-PL-12 (Targoff, I. N., et al., Am. J. Med. 88:241–251 (1990); and Friedman, A. W., et al., Semin. Arthritis Rheum. 26:459–467 (1996)), whereas none of 6 Japanese patients with anti-PL-12 antibodies fulfilled criteria for myositis (Hirakata, M., et al., Arthritis Rheum. 38:S321 (Abstract) (1995)). In the limited number of patients thus far observed, 2/10 anti-OJ patients had ILD without detectable myositis, and one had ILD with subclinical myositis.

Most sera with any of the five reported anti-synthetases specifically inhibit the aminoacylation of the respective tRNAs, indicating inhibition of the enzymatic function of the synthetase (Mathews, M. B., et al., Nature 304:177–179 (1983); Bunn, C. C., et al., J. Exp. Med. 163:1281–1291 (1986); Targoff, I. N., J. Immunol. 144:1737–1743 (1990); Targoff, I. N., et al., J. Immunol. 138:2874–2882 (1987); and Targoff, I. N., et al., Arthritis Rheum. 31:515–524 (1988)). For example, anti-Jo-l serum, IgG fraction, and affinity-purified IgG inhibit histidyl-tRNA synthetase activity and not that of other synthetases (Targoff, I. N., et al., J. Immunol. 138:2874–2882 (1987)). Only occasional anti-synthetase sera have been exceptions, i.e., did not inhibit (Targoff, I. N., et al., Am. J. Med. 88:241–251 (1990); and Targoff, I. N., et al., J. Clin. Invest. 91:2556–2564 (1993)). Such inhibition is not consistently seen with animal antisera raised against synthetases, and suggests that autoantibodies target an active site of the enzyme (Miller, F. W., et al., Proc. Natl. Acad. Sci. USA 87:9933–9937 (1990)). The identification of the previous 5 anti-synthetases was initially based on the demonstration that several sera that shared the same antibody, and immunoprecipitated the same tRNAs, could inhibit the same synthetase enzyme and not others (Mathews, M. B., et al., Nature 304:177– 179 (1983); Mathews, M. B., et al., J. Exp. Med. 160:420–434 (1984); Bunn, C. C., et al., J. Exp. Med. 163:1281–1291 (1986); Targoff, I. N., J. Immunol. 144:1737–1743 (1990); and Targoff, I. N., et al., Arthritis Rheum. 35:821–830 (1992)). Later, other methods were used to support these identifications, such as demonstration for anti-Jo-1 and anti-EJ of reaction with enzymatically active recombinant protein (Raben, N., et al., J. Biol. Chem. 269:24277–24283 (1994); and Ge, Q., et al., J. Biol. Chem. 269:28790–28797 (1994)).

Human autoimmune diseases related to AsnRS are currently undetected. There is a need for the detection of antibodies to this enzyme.

OBJECTS

It is therefore an object of the present invention to provide DNA encoding human asparaginyl-tRNA-synthetase. Further, it is an object of the present invention to provide vectors and cells containing the DNA and expressing the asparaginyl-tRNA synthetase. Further still, it is an object of the present invention to provide methods and test kits for diagnosing the presence of the human asparaginyl-tRNA synthetase antibodies, thereby indicating a possible autoimmune disorder. These and other objects will become increasingly apparent from the following description and the drawings.

SUMMARY OF THE INVENTION

The present invention relates to an essentially pure nucleic acid which encodes a human asparaginyl-tRNA synthetase.

The present invention relates to an essentially pure nucleic acid which codes for an active human asparaginyl-tRNA synthetase, and which hybridizes to DNA having SEQ ID NO:1 under moderate stringency conditions, wherein moderate stringency conditions comprise hybridization in 6×SSC, 1% sodium dodecyl sulfate, 20 mM $NaH_2PO_4$ and 500 $\mu$g/ml salmon sperm DNA at 42° C. for 16 hours and two washes in 6×SSC and 0.1% sodium dodecyl sulfate at 56° C. for 15 minutes.

The present invention relates to an essentially pure nucleic acid which encodes an amino acid sequence SEQ ID NO:2.

The present invention relates to an isolated nucleic acid comprising a nucleic acid having a sequence complementary to a DNA strand having a SEQ ID NO:1 or to an RNA counterpart of SEQ ID NO:1 or to a portion of said DNA or RNA counterpart comprising the SEQ ID NO:1.

The present invention relates to a recombinant nucleic acid vector comprising nucleic acid which encodes a human asparaginyl-tRNA synthetase and which hybridizes to DNA having SEQ ID NO:1 under moderate stringency conditions, wherein moderate stringency conditions comprise hybridization in 6×SSC, 1% sodium dodecyl sulfate, 20 mM $NaH_2PO_4$ and 500 $\mu$g/ml salmon sperm DNA at 42° C. for 16 hours and two washes in 6×SSC and 0.1% sodium dodecyl sulfate at 56° C. for 15 minutes.

The present invention relates to a recombinant nucleic acid vector comprising DNA which encodes a human asparaginyl-tRNA synthetase.

The present invention relates to an expression vector comprising a nucleic acid encoding a fusion protein comprising a human asparaginyl-tRNA synthetase, wherein said nucleic acid comprises a coding sequence for a human asparaginyl-tRNA synthetase, and wherein the coding sequence is under control of transcription signals and is linked to appropriate translation signals for expression in a suitable host cell.

The present invention relates to a host cell comprising a recombinant human asparaginyl-tRNA synthetase gene.

The present invention relates to a method for producing active human asparaginyl-tRNA synthetase comprising the following steps:

(a) constructing a recombinant nucleic acid vector comprising a coding sequence for human asparaginyl-tRNA synthetase, wherein the coding sequence is under the control of transcription signals and is linked to appropriate translation signals;

(b) introducing the vector into suitable host cells which support replication of the vector;

(c) maintaining the host cells under conditions in which the coding sequence for human asparaginyl-tRNA synthetase is expressed; and (d) isolating human asparaginyl-tRNA synthetase from the host cells.

The present invention relates to a method for producing isolated, recombinant human asparaginyl-tRNA synthetase comprising the following steps:

(a) providing host cells comprising a recombinant gene encoding human asparaginyl-tRNA synthetase;

(b) maintaining the host cells under conditions in which the gene encoding human asparaginyl-tRNA synthetase is expressed; and (c) isolating human asparaginyl-tRNA synthetase from the host cells.

The present invention relates to a host cell comprising a recombinant nucleic acid which encodes a human asparaginyl-tRNA synthetase and which hybridizes to DNA having SEQ ID NO:1 under moderate stringency conditions, wherein moderate stringency conditions comprise hybridization in 6×SSC, 1% sodium dodecyl sulfate, 20 mM $NaH_2PO_4$ and 500 µg/ml salmon sperm DNA at 42° C. for 16 hours and two washes in 6×SSC and 0.1% sodium dodecyl sulfate at 56° C. for 15 minutes.

The present invention relates to a compound screening assay method for an effect on synthetase activity which comprises:

(a) providing an isolated and purified full length, enzymatically active protein which comprises recombinant DNA derived human asparaginyl aminoacyl-tRNA synthetase in an aqueous solution with a compound to be tested for an affect on synthetase activity, asparaginyl and a t-RNA; and (b) determining the effect of said compound on synthetase activity.

The present invention relates to a process for asparaginyl aminoacylation of tRNA which comprises:

(a) contacting a mixture of protein containing tRNA and asparagine with an isolated and purified full length, enzymatically active recombinant DNA derived human asparaginyl aminoacyl-tRNA synthetase; and (b) aminoacylating the tRNA with asparagine.

The present invention relates to an assay for detection of an antibody related to an autoimmune disorder in a human which comprises:

(a) providing a biological sample from the human suspected of containing an antibody to human asparaginyl-tRNA synthetase;

(b) contacting the antibody with a recombinant DNA derived asparaginyl tRNA synthetase peptide comprising adjoining segments of motifs 1 and 2 so that the asparaginyl-tRNA synthetase peptide binds to the antibody in the sample; and (c) detecting the antibody bound to the asparaginyl-tRNA synthetase bound to the antibody in the sample.

The present invention relates to a kit for detection of an autoimmune disorder in a human biological sample which comprises:

(a) a container with a recombinant DNA derived asparaginyl t-RNA synthetase peptide comprising adjoining motifs 1 and 2 so that the asparaginyl-tRNA synthetase peptide can bind an antibody related to the autoimmune disorder in the sample; and (b) reagents for detecting the binding of the antibody to the asparaginyl-tRNA synthetase.

BRIEF DESCRIPTION OF DRAWINGS

FIGS. 1A and 1B are charts showing multiple alignment between prokaryotic and eukaryotic AsnRS sequences. The program PILEUP was used (GCG package, University of Wisconsin). The origins are (accession number in the SwissProt or EMBL data banks are indicated in parenthesis); Homo sapiens, hsAsnRS (AJ000334; SEQ ID NO: 2); *Brugia malayi*, bmAsnRS (P10723; SEQ ID NO:3); *Saccharomyces cerevisiae* scAsnRS (P38707; SEQ ID NO:4); *Thermus thermophilus*, ttAsnRS (X91009; SEQ ID NO:5). The position where the residues are strictly conserved in this alignment are in bold type. The Class II specific motifs are indicated by #. The N-terminal extensions characteristic for eukaryotic AsnRS sequences are boxed. Dashed lines indicate the putative β-barrel domain most probably involved in tRNA anticodon recognition.

(FIG. 2A) Coomassie-brilliant blue stained SDS gel (12% polyacrylamide). Lane 1, molecular mass marker; lane 2, bacterial control extract; lane 3, bacterial extract containing the recombinant calmodulin-binding protein (CBP) tagged protein; lane 4, purified hsAsnRSc. (FIG. 2B) Autoradiography of the western blot performed with the SDS gel showing the immunoreactivity of hsAsnRSc with anti-KS serum.

FIG. 6A shows the precipitin line formed between serum KS and HeLa cell extracts went through the lines of the Jo-1, PL-7, PL-12, and EJ system, indicating the immunologic distinctness of anti-KS from the previously described systems including the Jo-1, PL-7, PL-12, and EJ. (FIG. 6B) Furthermore, a line of immunologic identity was seen between serum KS, serum NI, and serum KN, confirming the presence of the same autoantibody in each serum, by immunodiffusion against HeLa cell extracts.

DESCRIPTION OF PREFERRED EMBODIMENTS

Figure 2A:
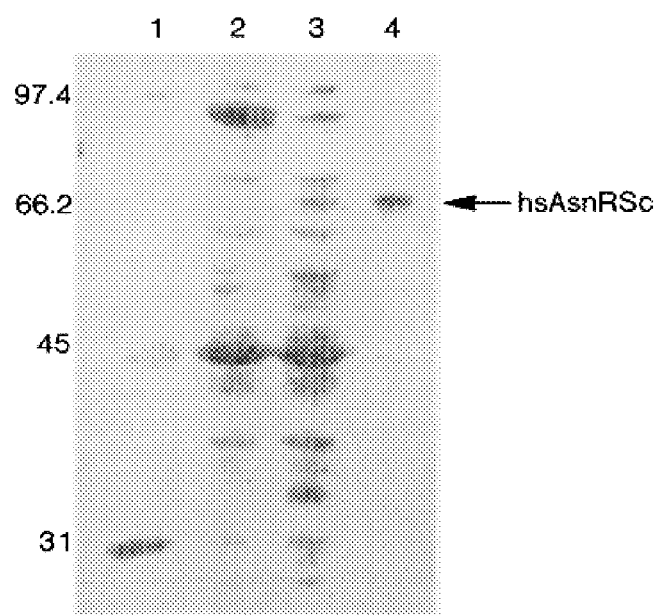
FIGS. 2A and 2B are gels showing expression in *E. coli*, purification and immunological reactivity with the anti-KS serum of the recombinant hsAsnRSc.

The cDNA for human cytosolic asparaginyl-tRNA synthetase (hsAsnRSc) was cloned and sequenced. The 1874 bp cDNA contains an open reading frame encoding 548 amino acids with a predicted $M_1$ of 62 938. The protein sequence has 58 and 53% identity with the homologous enzymes from *Brugia malayi* and *Saccharomyces cerevisiae* respectively (FIGS. 1A and 1B). The human enzyme was expressed in *Escherichia coli* as a fusion protein with a N-terminal 4 kDa calmodulin-binding peptide. A bacterial extract containing the fusion protein catalyzed the aminoacylation reaction of *S. cerevisiae* tRNA with $[^{14}C]$ asparagine at a 20-fold efficiency level above the control value confirming that this cDNA encodes a human AsnRS. The affinity chromatography purified fusion protein efficiently aminoacylated unfractionated calf liver and yeast tRNA but not *E. coli* tRNA, suggesting that the recombinant protein is the cytosolic AsnRS. Several human anti-synthetase sera were tested for their ability to neutralize hsAsnRSc activity. A human autoimmune serum (anti-KS) neutralized hsAsnRSc activity and this reaction was confirmed by western blot analysis. The human asparaginyl-tRNA synthetase appears to be like the alanyl- and histidyl-tRNA synthetases another example of a human Class II aminoacyl-tRNA synthetase involved in autoimmune reactions.

The present invention provides a diagnostic assay for detecting anti-hsAsnRSc antibodies in serum for determining whether a patient has the autoimmune disease associated with arthritis and interstitial lung disease without myositis. The diagnostic assay can be any of several solid phase immunoassays. An example of such a solid phase immunoassay is enzyme-linked immunosorbent assays (ELISA) developed by Engvall et al, Immunochem. 8: 871 (1971) and further refined by others such as Ljunggren et al J. Immunol. Meth. 88: 104 (1987) and Kemeny et al, Immunol. Today 7: 67 (1986). A 4 variation of the ELISA assay is disclosed in U.S. Pat. No. 5,079,172 to Hari et al which describes a diagnostic assay for detecting a first antibody using antigen coated spheres which is herein incorporated by reference. Other solid support diagnostic assays which are variations of the ELISA assay that are suitable for the present invention are immunodiagnostic assay such as those disclosed in PCT Application No. WO 88/08534 to May et al, PCT Application No. WO 91/12528 to Cole et al, PCT Application No. WO 90/15327 to Gould et al., U.S. Pat. No. 4,486,530 to David et al., and U.S. Pat. No. 4,786,589 to Rounds et al which are herein incorporated by reference.

In the ELISA-based assay of the present invention, anti-hsAsnRSc antibodies from serum from a patient form a complex with recombinant asparaginyl-tRNA synthetase on a surface with the synthetase immobilized to the surface prior to forming the antibody-antigen complex. Unbound antibodies are removed from the immobilized antibody-antigen complex by washing. The complex is then reacted with a second antibody that complexes with the first antibody to form a second complex consisting of an antigen, hsAsnRSc-antibody, second antibody complex. The second complex can be detected using a second antibody conjugated to horseradish-peroxidase or alkaline phosphatase. Alternatively, the second antibody can be conjugated to a fluorescing ligand, biotin, colored latex, colloidal gold magnetic beads, radioisotopes or the like.

The ELISA-based assay can be incorporated in a kit wherein a series of wells are coated with hsAspRCs. A second series of wells are coated with a non-reactive protein such as bovine serum albumen. The second series of wells serves as a negative control. A third series of wells is coated with human IgG. The third series of wells serves as a positive control for the detection method included with the kit. To test a serum sample, the serum is cleared of red blood cells by standard methods available in any medical laboratory. The serum is serially diluted from a range of neat to 1:1,000. An aliquot of each dilution is dispensed into separate wells of each of the first, second and third series of wells. The plate is incubated at room temperature for time sufficient for the antibody against hsAspRCs, if present in the serum, to form a complex with the recombinant hsAspRSc, usually 30 minutes to 2 hours. Afterwards, the wells are washed free of unbound antibodies and a ligand conjugated antibody is added to each well. The plate is incubated for approximately 30 minutes or more at room temperature. The unbound antibodies are washed from the wells. The hsAspRCs-serum antibody-ligand antibody complex is detected by a detection method suitable to detect the ligand. The ligand can be a color producing ligand such as alkaline phosphatase or horseradish peroxidase, or a fluorescing compound.

The present invention can be provided as a kit based on the dip-stick device as described in PCT Application No. WO 88/08534 to May et al., PCT Application No. WO 91/12528 to Cole et al., PCT Application No. WO 90/15327 to Gould et al., U.S. Pat. No. 4,486,530 to David et al., and U.S. Pat. No. 4,786,589 to Rounds et al. In this case the recombinant hsAspRCs is deposited as a line or dot on the membrane of the device. Serum applied to the device as disclosed in the patents diffuses through the membrane. If the serum contains antibodies against hsAspRCs, the antibodies will form a complex with the hsAspRCs on the membrane. Detection is by a calorimetric method incorporated into the device or by immersing the device into a solution that causes a calorimetric reaction.

*Escherichia coli* containing a vector encoding human asparaginyl-tRNA synthetase will be deposited with the American Type Culture Collection, 10801 University Blvd., Manassas, Va. 20110-2209 under the Budapest Treaty on Nov. 8, 2000 as accession no. ATCC PTA-2657. DNA and synthetase encoded by DNA is deposited with GenBank as accession no. AJ000334.

For purposes of promoting a further understanding of the present invention, the following examples are provided, which are illustrative only.

EXAMPLE 1

Materials and Methods

Restriction endonucleases, modification enzymes and unfractionated tRNAs were purchased from Boehringer Mannheim. Oligonucleotides were supplied by Genosys. Autoimmune sera (anti-HisRS, anti-AlaRS, anti-KS) were kindly provided by Dr. I. Targoff (Oklahoma Research Foundation) and Dr. M. Hirakata (University of Tokyo School of Medicine).

Cloning of hsAsnRSc cDNA

Molecular cloning methods were used according to Sambrook et al (Sambrook, J., et al., Molecular Cloning: A Laboratory Manual. Cold Spring Harbour Laboratory Press, NY (1989)). Human Expressed Sequence Tag (EST) sequences coding for peptides showing strong sequence similarities with *Brugia malayi* AsnRS were aligned. Missing 5' and 3' regions were amplified by PCR methods on human liver 5' RACE-Ready cDNA from Clontech. Thirty cycles of amplification were carried out (20 s denaturation at 94° C., 30 s annealing at 60–68° C. and 5 minutes elongation at 68° C.). The complete cDNA was amplified using the 5' RACE-Ready cDNA with the oligonucleotide primer 5'-CCGGATCCCATATGGTGCTAGCAGAGCTGT-3' (SEQ ID NO:6) (restriction sites are in bold and modified nucleotides are underlined) creating a BamHI (and NdeI) restriction site for cloning the AsnRS cDNA fragment into the pCal-n expression vector (Clontech) and the oligonucleotide 5'-TCAGGTGATTTGAGATAGTTTTT-ATGG-3' (SEQ ID NO: 7).

Cloning and Sequencing of the Human AsnRS CDNA (EMBL Database: Aj000334)

Human EST sequences coding for peptides which show strong sequence similarities with *B. malayi* AsnRS were aligned to a 1302 bp fragment. The assembled cDNA sequence comprises 1874 bp with a large predicted open reading frame of 1644 bp. This encodes a protein of 548 amino acids with a predicted $M_r$ of 62 938. Sequence alignment of several bacterial and eukaryotic AsnRSs indicates that the human enzyme is composed of three characteristic domains; a N-terminal extension, typical for eukaryotic AsnRS, followed by a putative β-barrel domain probably involved in tRNA$^{ASn}$ anticodon recognition and a catalytic domain containing the three Class II specific motifs (FIGS. 1A and 1B).

EXAMPLE 2
Bacterial Expression and Purification of the Recombinant Enzyme

Figure 2B:
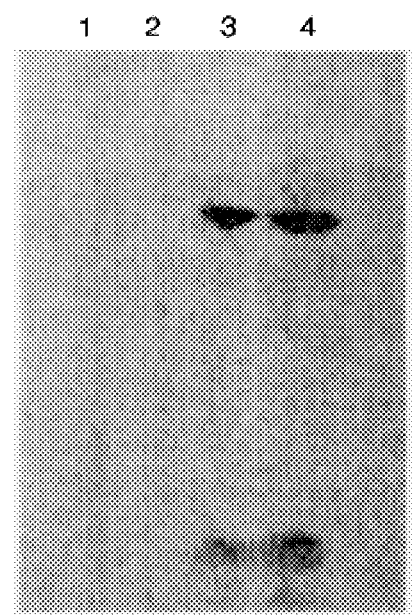

The recombinant protein comprises a N-terminal 4 kD. Calmodulin Binding Peptide (CBP) fusion tag coupled to the AsnRS. FIGS. 2A and 2B show the SDS-PAGE analysis of the AsnRS fusion protein in an unfractionated bacterial extract (lane 3) and its purified form (lane 4). The apparent molecular weight of the fusion protein is in agreement with the predicted molecular weight of AsnRS (63+4 kDa CBP).

Unfractionated bacterial extracts were assayed for their ability to catalyze the aminoacylation of *S. cerevisiae* tRNA with [$^{14}$C]asparagine; these extracts had 20-fold greater aminoacylation activity with *S. cerevisiae* tRNA relative to *E. coli* extracts carrying only the pCal-n vector.

Bacterial extracts were loaded on a calmodulin column in the presence of calcium. EGTA eluted fractions were collected and analyzed by western blot methods for the presence of *E. coli* AsnRS contamination using a rabbit anti-*E. coli* AsnRS serum (data not shown).

Figure 3:
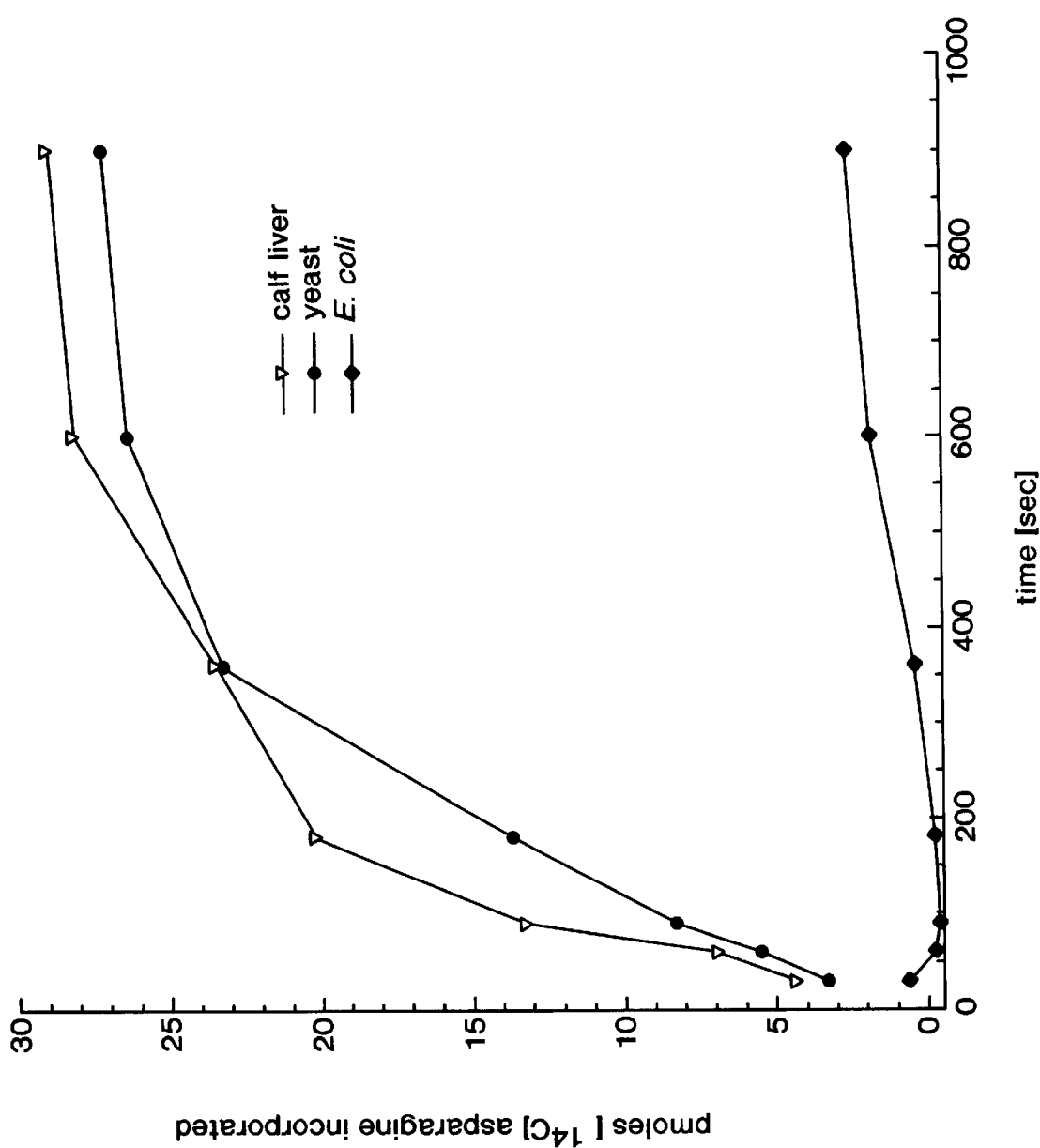
FIG. 3 is a graph showing asparaginyl-tRNA synthetase activity of the recombinant human enzyme with tRNA from different sources. Incorporation by the purified enzyme (33 nM) of [$^{14}$C] asparagine (pmol) into unfractionated tRNA from *E. coli* (♦), from yeast (●) and from calf liver (V).

EXAMPLE 3
Aminoacylation Activity of the Recombinant Human AsnRS using tRNA from Different Origins The purified AsnRS fusion protein was tested for its enzymatic activity with tRNA substrates of different origins, i.e. *E. coli*, *S. cerevisiae* and calf liver at the same relative concentration of tRNAASn. FIG. 3 shows that calf liver and *S. cerevisiae* tRNAs are both efficient substrates for the human enzyme. For both tRNAs similar plateau values are reached although the initial rate is somewhat higher for the calf liver tRNA (0.15 pmol/s$^{-1}$ compared to 0.09 pmol/s$^1$ for *S. cerevisiae* tRNA).

EXAMPLE 4
Neutralization of AsnRS Activity by a Human Autoimmune Serum

The AsnRS fusion protein was preincubated with the different autoimmune sera (anti-KS, anti-AlaRS and anti-HisRS) and two control sera. After preincubation, residual aminoacylation activity was determined. Only the anti-KS serum neutralized the human AsnRS activity significantly with an inhibition of 98%. The other anti-synthetase sera (anti-HisRS and anti-AlaRs) did not neutralize significantly the enzyme activity (<4% of inhibition).

EXAMPLE 5
Immunoreactivity of the Anti-KS Serum in a Western Blot Experiment

Since only the anti-KS serum produced significant inhibition of AsnRS activity the interaction of this serum with recombinant protein was examined by western blot analysis. Samples of bacterial extract from the overproducing strain containing recombinant synthetase and a control strain containing only the pCal-n vector together with purified human AsnRS fusion protein were loaded on a SDS-polyacrylamide gel. After electrophoresis, the proteins were transferred to a nylon membrane and incubated with a human anti-KS serum. Antigen-antibody interactions were detected using $^{35}$S-labeled protein A. FIGS. 2A and 2B show that the human anti-KS serum specifically interacts with the human AsnRS both in the bacterial extract and in purified form.

EXAMPLE 6
Expression of hsAsnRS as a Bacterial Fusion Protein and Purification

The hsAsnRSc coding region was inserted into pCal-n vector which encodes a calmodulin-binding peptide (CBP) (Zheng, C. E., et al., Gene 186:55–60 (1997)) as a BamHI-EcoRI fragment and transformed into the *Escherichia coli* strain BL21 (DE3) to produce a vector, pCalhsAsnRSc, which encodes a human asparaginyl-tRNA synthetase fused to CBP. Cells were grown in LB at 37° C. to an $A_{600}$ of 0.6, isopropyl-1thio-β-D-galactoside was added to a final concentration of 0.2 mM and incubation at 23° C. continued for a further 3 hours. Cells were lysed by lysozyme and sodium deoxycholate treatment (Leberman, R., et al., Anal. Biochem. 104:29–36 (1980)).

EXAMPLE 7
Aminoacylation Assay and Kinetic Parameters

The aminoacylation reaction assay was as previously described (Vincent, C., et al., Nucleic Acids Res. 23:1113–1118 (1995)) in the presence of 1.12 μM tRNA$^{Asn}$ of unfractionated tRNA from *E. coli* MRE600, *Saccharomyces cerevisiae* or calf liver; the determination of asparagine acceptance activity in unfractionated tRNA and *E. coli* was performed with an *E. coli* protein extract, that in unfractioned *S. cerevisiae* and calf liver tRNA with hsAsnRSc fusion protein. The concentration of recombinant human AsnRS was 33 nM.

EXAMPLE 8
Neutralization Assay

AsnRS (66 nM) was preincubated for 10 minutes on ice with the various.sera (1:10 dilution of the sera donated by Drs. Targoff and Hirakata). After preincubation the aminoacylation activity was determined using calf liver tRNA. In the aminoacylation reaction the sera are present in a 1:100 dilution.

EXAMPLE 9
Detection of the Recombinant hsAsnRSc by Western Blot Using Autoimmune Serum (anti-KS).

Protein samples were separated electrophoretically on a 12% SDS-polyacrylamide gel and transferred to a Immobilon-P membrane for western blot analysis (Towbin, H., et al., Proc. Natl. Acad. Sci. USA 76:4350–4354 (1979)). The immunological reactivity of the recombinant hsAsnRSc was tested against 5.0 μl human anti-KS serum. [$^{35}$S] protein A (16.7 mM. 600 Ci/mmol; Amersham) was used to detect specific AsnRS-antibody interactions by autoradiograph (FIGS. 2A and 2B) after 16 hours exposure to Biomax film (Kodak).

The cDNA coding for the complete human AsnRS was isolated. This provides the first example of a mammalian AsnRS sequence. The sequence exhibits a high degree of similarity with the two other known eukaryotic AsnRSs: a 58% amino acid identity with the AsnRS from *B. malayi* and a 53% identity with that from *S. cerevisiae*.

Based on the following observations we conclude that the sequence we have determined is that of human cytosolic AsnRS: (i) the absence of a mitochondrial import signal, (ii) strong sequence similarities to the cytosolic AsnRSs from *B. malayi* and *S. cerevisiae* and weaker similarities with bacterial enzymes, (iii) estimated moelcular weight and calculated isoelectric point is typical for a cytosolic AsnRS, (iv) calf liver and *S. cerevisiae* tRNA are significantly better substrates than *E. coli* tRNA.

Despite a similar degree of overall sequence identity of human tRNA compared to tRNA from *E. coli* (62%) or from *S. cerevisiae* (65%), *E. coli* tRNA is poorly aminoacylated by the hsAsnRSc fusion protein in contrast to its *S. cerevisiae* counterpart. This could be due to one base insertion into the D-loop of the eukaryotic tRNA$^{ASn}$ at position 21 (Sprinzl, M., et al., Nucleic Acids Res. 24:68–72 (1996)).

Some eukaryotic synthetases are involved in pathological conditions (Targoff, I. N., Invest. Dermatol. 100: 116S–123S (1993)). Patients with systemic autoimmune diseases make specific autoantibodies that are directed against self structures. According to one hypothesis, these autoantibodies arise through an immune response to foreign antigens such as infectious agents that share, by molecular mimicry, common structures with host proteins. Autoantibodies are found in most patients with polymyositis or dermatomyositis and 35–40% of these patients have myositis-specific antibodies. 25–30% of these patients have antibodies raised against aminoacyl-tRNA synthetases, of which anti-Jo-1, directed at histidyl-tRNA synthetase (His/RS) is by far the most common (Targoff, I. N., Invest. Dermatol. 100:116S-123S (1993)).

Of the several autoimmune sera tested for their capacity to neutralize the hsAsnRSc activity, only the anti-KS autoimmune serum isolated by Dr. M. Hirakata was able to neutralize the activity of the recombinant hsAsnRSc. The other anti-synthetase sera (anti-AlaRS and anti-HisRS) did not show any significant inhibition. Besides its neutralizing activity, the anti-KS serum was also able to recognize the recombinant AsnRS fusion protein on an immunoblot. It has been shown that anti-Jo-1 antibodies recognize multiple conformation-dependent and independent epitopes on human HisRS and that auto-epitopes vary among different myositis patients (Ramsden, D. A., et al., J. Immunol. 143:2267–2272 (1989)). Furthermore, it has been demonstrated that the substrates ATP and histidine act as competitive inhibitors for the formation of the synthetase-anti-Jo-1 antibody complex, whereas the tRNA acts in a non-competitive way (Fahoum, S. K., et al., Biochemistry 26:5871–5877 (1987)). The human AsnRS has yet to be characterized for this complex formation.

Autoantibodies of several aminoacyl-tRNA synthetases (those for alanine, glycine, histidine, isoleucine, and threonine) have been described and all have been associated with the similar syndrome of myositis (polymyositis and dermatomyositis), interstitial lung disease, arthritis and other features. Recently anti-KS a novel autoantibody to asparaginyl-tRNA synthetase was isolated from a patient who had arthritis and interstitial lung disease but no polymyositis (Hirakata, M., et al., Arthritis Rheum. 39(8) Suppl. S39 (1996)). We have cloned and sequenced the cDNA for human cytosolic asparaginyl-tRNA synthetase (hsAsnRSc). The cDNA contains an open reading frame encoding 548 amino acids with a predicted $M_r$ of 62 938. The protein sequence has 58% and 53% identity with the homologous enzymes from the nematode *Brugia malayi* and *Saccharomyces cerevisiae*, respectively. The human enzyme was expressed in *Escherichia coli* as a fusion protein with a N-terminal calmodulin-binding peptide. A bacterial extract containing the fusion protein catalyzed the aminoacylation reaction of *S. cerevisiae* tRNA with [$^{14}$C] -asparagine at a 20 fold efficiency level above the control value confirming that this cDNA encodes a human AsnRS. The purified fusion protein efficiently aminoacylated unfractionated calf liver and yeast tRNA but not *E. coli* tRNA, suggesting that the recombinant protein is the cytosolic AsnRS. Several human anti-synthetase sera (anti-alanine, anti-histidine and anti-asparagine) were tested for their ability to neutralize hsAsnRSc activity. Only the human anti-asparaginyl autoimmune serum (anti-KS) neutralized hsAsnRSc activity and this reaction was confirmed by western-blot analysis. Taking advantage of the knowledge of the crystallographic structure of the *Thermus thermophilus* homologous enzyme (Berthet-Colominas, C., et al., EMBO J., 17:2947–2960 (1998)) mutants of the human enzyme were designed which contain different domains (eukaryote specific domain, β-barrel domain, catalytic domain, etc.) in order to identify the part(s) of the protein recognized by the autoantibodies. The mutant protein were tested for enzymatic activity and for immune reactivity with the anti-KS serum. Heat denaturation studies on the recombinant protein show that ELISA reactivity is lost after heating to 55° C. indicating that the major epitopes are conformational. The human asparaginyl-tRNA synthetase appears to be like the alanyl- and histidyl-tRNA synthetases another example of a human Class II aminoacyl-tRNA synthetase involved in autoimmune reactions.

Autoantibodies to five of the aminoacyl-transfer RNA (tRNA) synthetases are associated with a syndrome of inflammatory myopathy with interstitial lung disease (ILD) and arthritis. Serum KS, from a patient with ILD and inflammatory arthritis without evidence of myositis, immunoprecipitated a tRNA that was distinct from that precipitated by any described anti-synthetase or other reported tRNA-related antibodies, along with a protein of 65 kDa. KS serum and IgG fraction each showed significant (88%) inhibition of asparaginyl-tRNA synthetase (AsnRS) activity, but not of any of the other 19 aminoacyl-tRNA synthetase activities. Among 884 patients with connective tissue diseases tested, only 2 other sera were found to immunoprecipitate tRNAs and proteins of identical gel mobility. These 2 and KS showed identical immunodiffusion lines using HeLa cell extract. The new sera significantly inhibited AsnRS without significant effects on other synthetases tested. Both patients had ILD, but neither had evidence of myositis. These data strongly suggest that these three sera have autoantibodies to AsnRS, representing a sixth anti-synthetase. Anti-KS was more closely associated with ILD than with myositis. Further study of this antibody might prove useful in dissecting the stimuli responsible for the genesis of anti-synthetase autoantibodies.

EXAMPLE 10

Materials and Methods

Sera. Serum samples were obtained from 884 patients with connective tissue diseases followed in clinics at Keio University in Tokyo, and Kyoto University in Kyoto, Japan. These included 114 with PM/DM, 392 with SLE, 200 with systemic sclerosis (SSc), 56 with rheumatoid arthritis (RA) and 102 patients with ILD not meeting criteria for other conditions. Stored sera known to contain autoantibodies against synthetases for histidine, glycine, alanine and threonine were used as controls.

Immunoprecipitation. Immunoprecipitation (IPP) from HeLa cell extracts was performed as previously described (Targoff, I. N., J. Immunol. 144:1737–1743 (1990); and Hirakata, M., et al., Arthritis Rheum. 35:449–456 (1992)). 10 µl of patient sera was mixed with 2 mg of Protein A-Sepharose CL-4B (Pharmacia Biotech, AB., Uppsala, Sweden) in 500 µl of IPP buffer (10 mM Tris HCl at pH 8.0, 500 mM NaCl, 0.1% Nonidet P-40) and incubated with end-over-end rotation (Labquake shaker; Lab Industries, Berkeley, Calif.) for 2 hours at 4° C. The IgG-coated Sepharose was washed 4 times in 500 µl of IPP buffer using 10-second spins in a microfuge tube, and resuspended in 400 µl of NET-2-buffer.

For analysis of RNAs, this suspension was incubated with 100 µl of extracts, derived from $6 \times 10^6$ cells, on the rotator for 2 hours at 4° C. The antigen-bound Sepharose was then collected with a 10-second centrifugation in the microfuge, washed 4 times with NET-2 buffer and were resuspended in 300 µl of NET-2 buffer. To extract bound RNAs, 30 l of 3.0 M sodium acetate, 30 µl of 10% sodium dodecyl sulfate, 2 µl of carrier yeast tRNA (Sigma 10 mg/ml) and 300 µl of phenol/chloroform/isoamyl alcohol (50:50:1; containing 0.1% 8-hydroxyquinoline) were added to the Sepharose beads. After agitation in a Vortex mixer and spinning for 1 minute, RNAs were recovered in the aqueous phase after ethanol precipitation, and dissolved in 20 µl of electrophoresis sample buffer, composed of 10 M urea, 0.025% bromophenol blue and 0.025% xylene cyanol-FF in TBE buffer (90 mM Tris-HCl at pH 8.6, 90 mM boric acid, and 1 mM EDTA). The RNA samples were denatured at 65° C. for 5 minutes and then resolved in 7 M urea-10% polyacrylamide gel, which was stained with silver (Bio-Rad Laboratories, Hercules, Calif.). In certain experiments, cell extracts ($6 \times 10^6$ cells/sample) were deproteinized with phenol/chloroform/isoamyl alcohol prior to IPP, and tested in parallel with untreated extracts.

For protein studies, antibody-coated Sepharose was mixed with 400 µl of $^{35}$S-methionine-labeled HeLa extract derived from $2 \times 10^5$ cells, and rotated at 4° C. for 2 hours. After 4 washes with IPP buffer, the Sepharose was resuspended in SDS-sample buffer (2% SDS, 10% glycerol, 62.5 mM Tris-HCl at pH 6.8, 0.005% bromophenol blue). After heating (90° C. for 5 minutes), the proteins were fractionated by SDS-10% PAGE gels, enhanced with 0.5 M sodium salicylate, and dried. Labeled proteins were analyzed by autoradiography. Aminoacylation. Aminoacylation reactions were performed as described previously (Targoff, I. N., J. Immunol. 144:1737–1743 (1990); and Targoff, I. N., et al., J. Clin. Invest. 84:162–172 (1989)). Results of inhibition testing with sera were expressed as the percent inhibition of the average activity seen with 2 normals; i.e., % inhibition= [(Average cpm with normal serum)−(cpm with test serum)]× 100/(Average cpm with normal serum). Inhibition of >50% compared with the average activity of normal serum was considered significant. Purification of the KS antigen. Affinity chromatography was performed as previously described (Targoff, I. N., et al., J. Clin. Invest. 84:162–172 (1989)). The KS antigen was purified from HeLa cell extracts. IgG fraction was purified from 20 ml of KS serum using DEAE. KS IgG was coupled to Affi-gel (Bio-Rad Laboratories, Richmond, Calif.) hydroxysuccinamide-agarose in 0.1 M bicarbonate buffer at pH 8.3, with >90% coupling. The immunoadsorbent was washed extensively, including with the intended eluting agent (3 M $MgCl_2$). Later experiments were performed using a second column prepared in a similar manner. After HeLa extract was applied to the column in excess of adsorbing capacity, the column was extensively washed with 0.5 M NaCl in 0.05 M Tris buffer at pH 7.2 with 0.01 M Na azide and 0.1 mM PMSF, and eluted with 3 M $MgCl_2$.

Other. Ouchterlony double immunodiffusion was performed as described previously using HeLa cell extract as antigen (Hirakata, M., et al., Arthritis Rheum. 35:449–456 (1992)). The IgG fraction of the patient sera was purified by DEAE chromatography.

Cases

Case 1.

In April of 1979 (at age 36), patient KS developed a no-productive cough and shortness of breath. Chest radiography showed interstitial fibrosis, and pulmonary function testing revealed a restrictive pattern. A diagnosis of ILD was made, and prednisolone 40 mg/day was begun, resulting in dramatic improvement of respiratory symptoms. In the autumn of 1980, inflammatory arthritis developed, treated with aspirin. In 1988, she was admitted to Keio University Hospital because of worsening polyarthritis and pulmonary hypertension due to fibrosis of both lower lung fields. No muscle weakness was found, and the creatine kinase level was normal (49 IU/l). Neither Raynaud's phenomenon nor elevation of creatine kinase occurred at any point in her course.

Case 2.

In 1990 (at age 61), patient NI noticed slight dyspnea on exertion. In 1991, her chest radiograph showed bilateral interstitial fibrosis in the lower lung fields, but she did not develop any other symptoms. The following year, a diagnosis of usual interstitial pneumonitis was made on the basis of open lung biopsy. She did not have any muscle weakness, elevation of the creatine kinase level, arthritis or Raynaud's phenomenon.

Case 3.

In 1966 (at age 44), patient KN was found to have a reticular pattern on her chest radiograph, but was followed up without treatment. In 1968, she noticed dyspnea on exertion and fatigability. In 1983, at age 61, she developed Raynaud's phenomenon. At age 64, open lung biopsy was performed, with histology showing usual interstitial pneumonitis, but she did not satisfy criteria for any connective tissue diseases.

RESULTS

Identification of a New tRNA-related Antibody.

Figure 4:
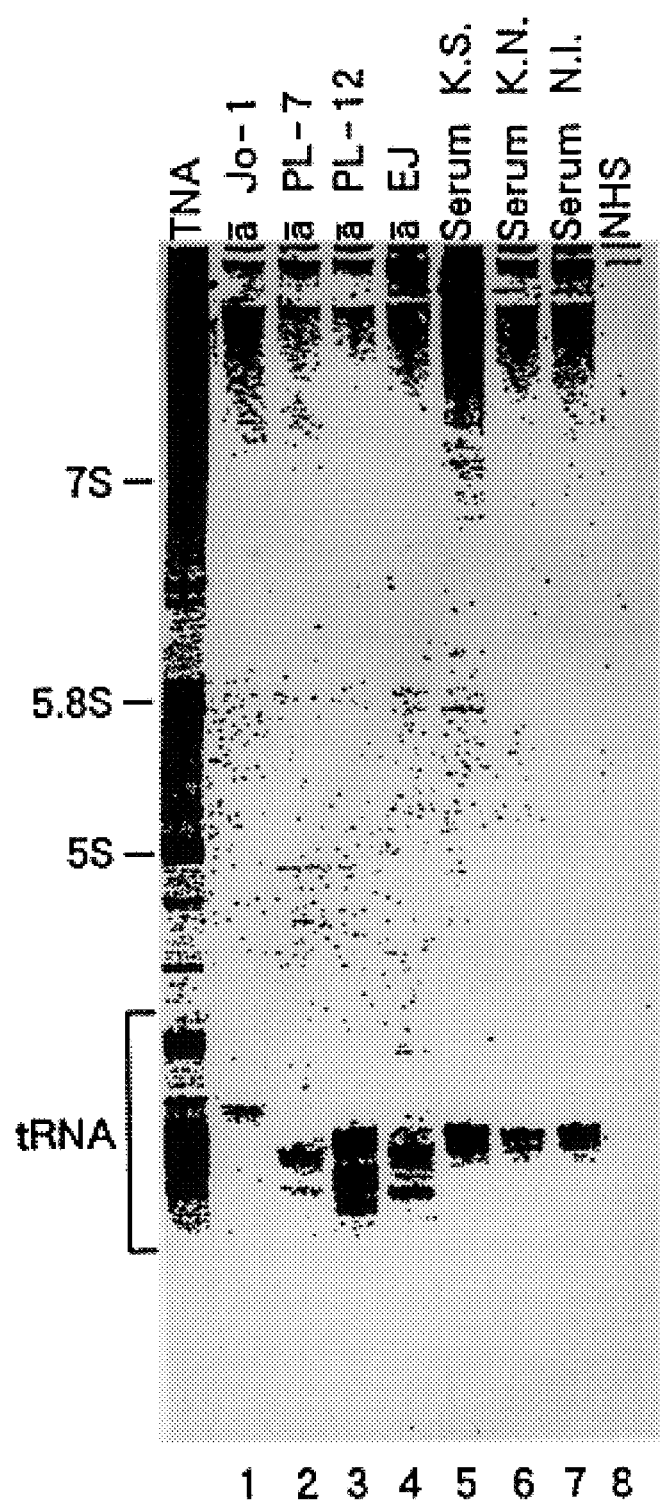
FIG. 4 is a gel showing immunoprecipitation for nucleic acids with anti-KS sera and controls. 7M Urea, 10% PAGE of phenol-extracted immunoprecipitates from HeLa cell extract, developed with silver stain. TNA=Total nucleic acids, with the 5.8 and 5.0 S small ribosomal RNAs and the tRNA region indicated. Sera used for immunoprecipitation include: Lanes 1–4=anti-synthetase sera indicated, with antibodies to Jo-1 (histidyl-tRNA synthetase), PL-7 (threonyl-tRNA synthetase), PL-12 (alanyl-tRNA synthetase), EJ (glycyl-tRNA synthetase); Lanes 5–7 =anti-KS sera as indicated; Lane 8=control serum indicated (NHS=normal human serum). The tRNA pattern with anti-KS sera is easily distinguishable from that of other anti-synthetases. The tRNA pattern with anti-OJ (isoleucyl-tRNA synthetase) is also easily distinguished (data not shown).

Serum of patient KS was found to immunoprecipitate a strong predominant nucleic acid band of tRNA size, accompanied by a weaker, faster band (FIG. 4, lane 5). This gel pattern of tRNAs was clearly distinguishable from the pattern of tRNAs precipitated by the five described antisynthetases (shown in FIG. 4 for four), or that associated with other identified tRNA-related autoantibodies. The predominant band was faster in migration than the Jo-1 RNA, and slower than the four major PL-12 bands. The additional weaker, faster band was almost identical in migration to the slowest band of the PL-12 RNAs. This serum also immunoprecipitated a very strong protein band from [$^{35}$S]-methionine-labeled HeLa cell extracts (FIG. 5, lane 5) migrating at 65 kDa that was clearly different from the bands immunoprecipitated by sera with the described antisynthetases (shown in FIG. 5 for four). A second, much fainter band was seen at 63 kDa.

Serum KS showed a line by immunodiffusion against HeLa cell extract that was non-identical with that of anti-Jo-1, anti-PL-7, anti-PL-12, and anti-EJ (FIG. 6).

Figure 5:
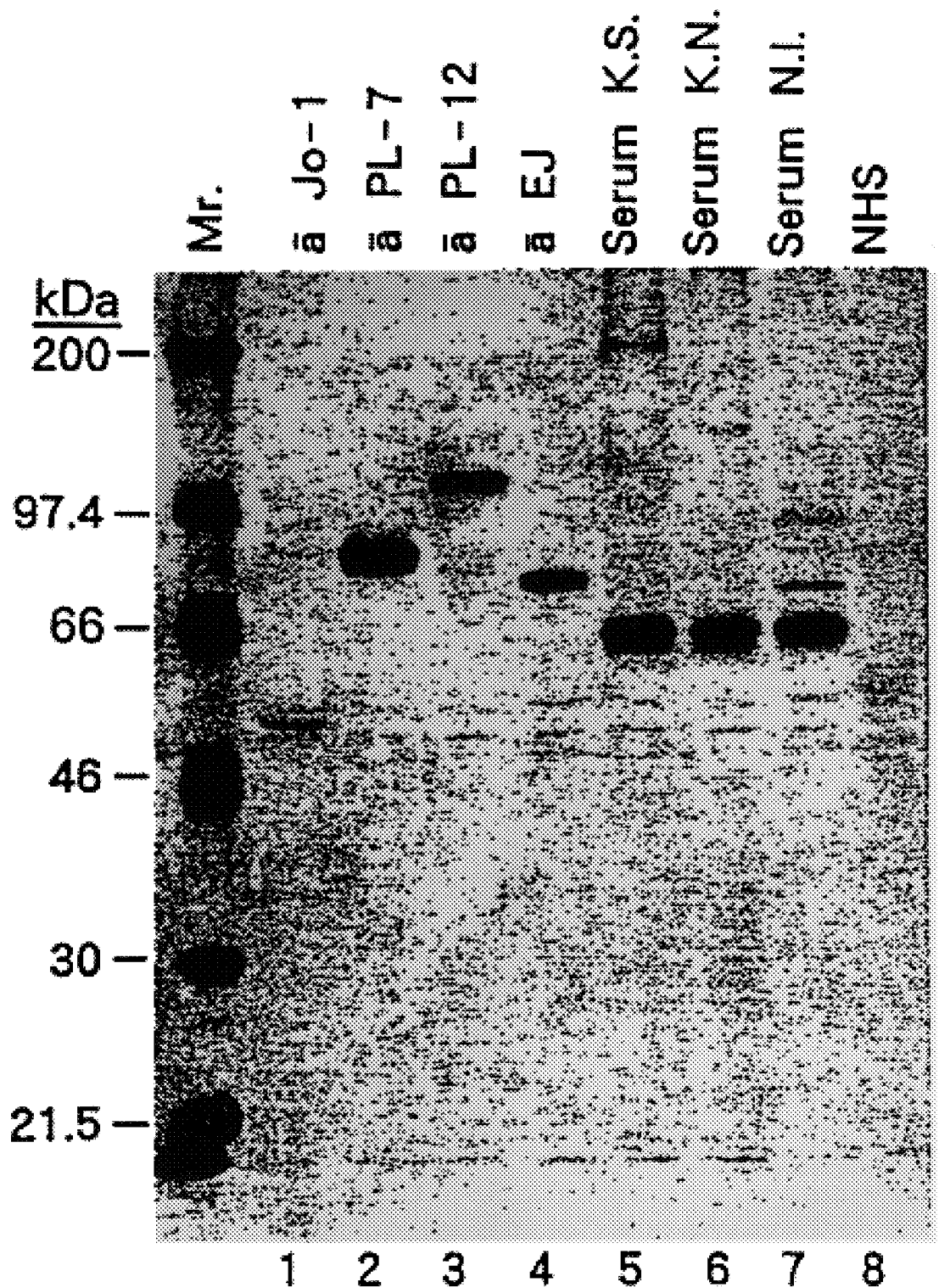
FIG. 5 is a gel immunoprecipitation for proteins with anti-KS sera and controls. Autoradiogram of 106 SDS-PAGE of immunoprecipitate from $^{35}$S-methionine-labeled HeLa cell extract. Mr.=Molecular weight markers, of the sizes indicated to the left in kDa (kilodaltons). The sera used for immunoprecipitation are the same as those in FIG. 4. The 65 kDa KS protein is easily distinguished from that of the anti-synthetases. Anti-OJ, which immunoprecipitates the multiple proteins of the synthetase complex in a distinctive pattern, would be easily distinguishable (data not shown).
Figures 6A, 6B:
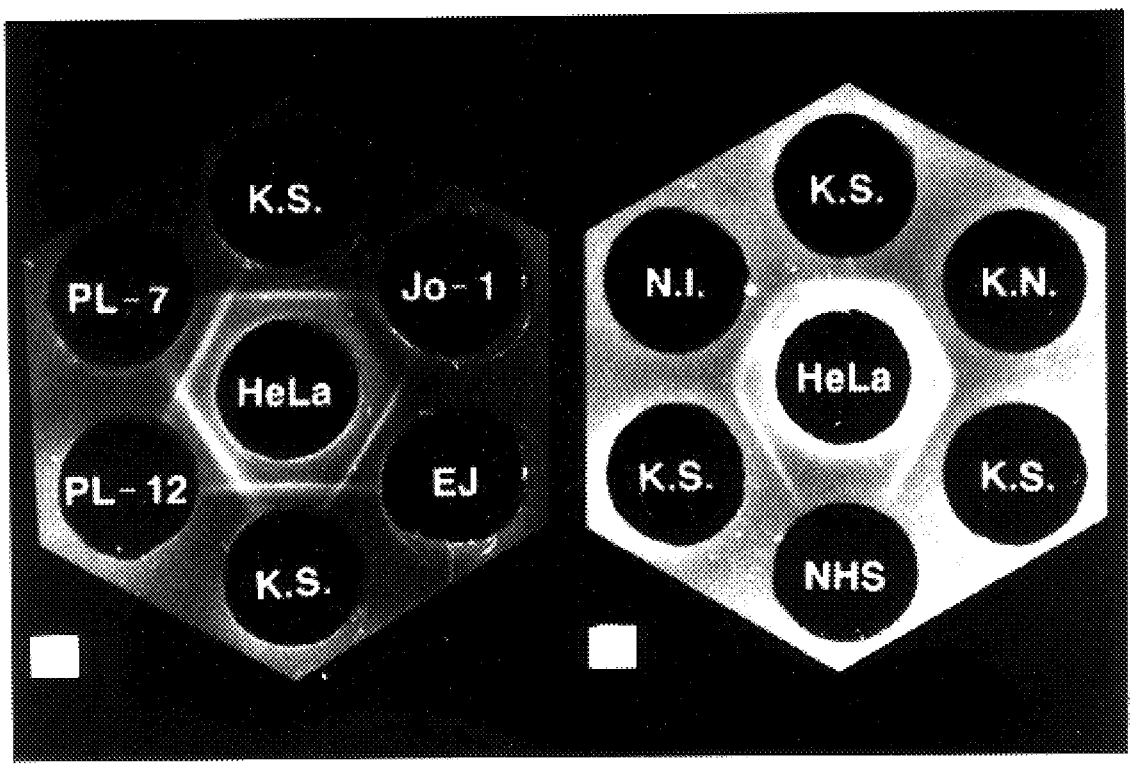
FIGS. 6A and 6B are gels showing ouchterlony double immunodiffusion of anti-KS sera and other anti-aminoacyl tRNA synthetase sera.
Figure 7:
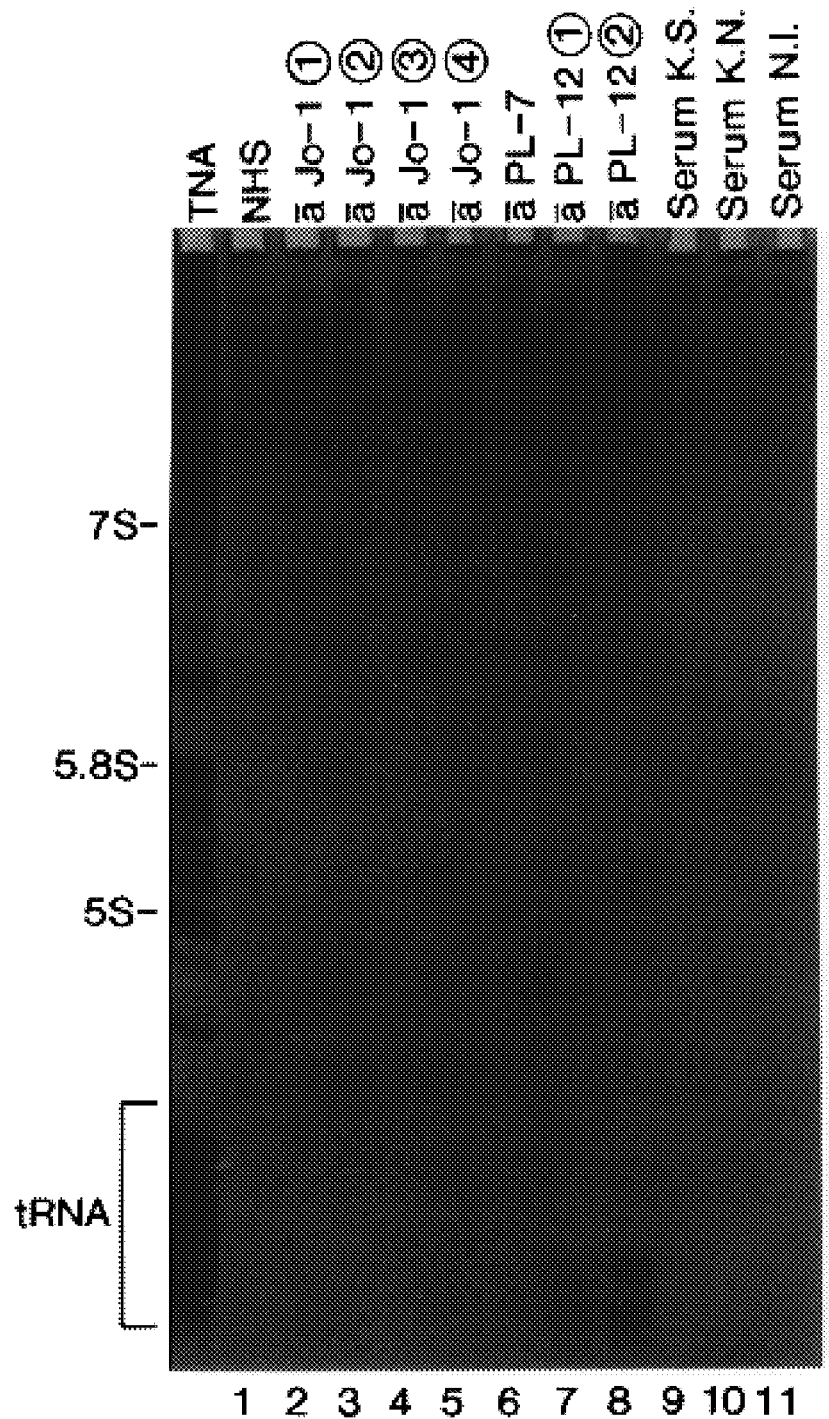
FIG. 7 is a gel showing immunoprecipitation with anti-KS sera and controls for nucleic acids after deproteinization of the HeLa cell extracts. TNA=Total nucleic acids with the 5.8 and 5.0 S small ribosomal RNAs and the tRNA region indicated. None of three anti-KS sera (lanes 9–11), anti-Jo-1 sera (lanes 2–5), or anti-PL-7 serum (lane 6) immunoprecipitated any RNA after deproteinization of the HeLa cell extracts, whereas control anti-PL-12 sera (lanes 7,8) consistently precipitated the PL-12 tRNA pattern from the deproteinized extract.

Of 884 patients with connective tissue diseases or ILD and controls, sera from two other patients with ILD (NI and KN) immunoprecipitated tRNA bands that were identical to those of serum KS each time they were analyzed (FIG. 4, lanes 6, 7). Both of these sera immunoprecipitated strong 65 kDa protein bands that were also identical to that of serum KS, along with a faint 63 kDa band (FIG. 5, lanes 6, 7). Furthermore, by immunodiffusion against HeLa cell extracts, a line of immunologic identity was seen between serum KS, serum NI, and serum KN, confirming the presence of the same autoantibody in each serum (FIG. 6B). Thus, anti-KS antibodies were found in. 0.34% of patients with connective tissue disease and 2.94% of patients with ILD.

None of these three sera immunoprecipitated any RNA after deproteinization of the HeLa cell extracts, whereas control anti-PL-12 sera consistently precipitated the PL-12 tRNA pattern from the deproteinized extract (FIG. 4). This indicates that anti-KS did not directly bind tRNAs and the proteins of the KS antigen were required for antigenicity.
Identification of the KS Antigen.

IPP of a unique tRNA and a strong protein band by anti-KS suggested the possibility that it was a new anti-synthetase. This was assessed by testing KS serum for the ability to inhibit each of the 20 aminoacyl-tRNA synthetases in turn. The enzyme source, HeLa cell extract, was preincubated with serum, at a 1:100 final concentration in the reaction mixture, before using the extract in an in vitro aminoacylation assay. Significant (>50%) inhibition of asparaginyl-tRNA synthetase (AsnRS) was seen, with inhibition of 88% of the activity seen when normal serum was added, but there was no significant inhibitory effect on other aminoacyl-tRNA synthetases (range <0–29%) (Table I).

TABLE 1

Inhibition of Aminoacylation
Reactions for 20 amino acids by KS serum and IgG

| Amino Acid | NHS 1:10 | NI-IgG 6 mg/ml | KS serum 1:10 | KS IgG 6 mg/ml | Relevant* Synthetase |
|---|---|---|---|---|---|
| Alanine | 0 | 2 | 0 | 0 | 91 |
| Arginine | 0 | 0 | 4 | 0 | — |
| Asparagine | 0 | 14 | 88 | 88 | — |
| Aspartic Acid | 0 | 3.3 | 20 | 0 | — |
| Cysteine | 1.4 | 0 | 7.1 | 0 | — |
| Glutamic Acid | 0 | 0 | 3 | 0 | — |
| Glutamine | 0 | 0 | 19 | 0 | — |
| Glycine | 0 | 0 | 0 | 0 | 89 |
| Histidine | 0 | 0 | 0 | 0 | 98.9 |
| Isoleucine | 0 | 0 | 0 | 0 | 66 |
| Leucine | 0 | 0 | 3.4 | 0 | — |
| Lysine | 0 | 24 | 5 | 7.8 | 94.8 |
| Methionine | 0 | 24 | 1 | 16 | — |
| Phenylalanine | 0 | 17 | 0 | 7 | — |
| Proline | 0 | 0 | 0 | 0 | — |
| Serine | 0 | 30 | 6 | 15 | — |
| Threonine | 0 | 14 | 0 | 5.8 | 48.3 |
| Tryptophan | 0 | 8 | 29 | 4 | — |
| Tyrosine | 0 | 20 | 0 | 0 | — |
| Valine | 0 | 0 | 4 | 0 | — |

The percent inhibition of each of the aminoacylation reactions as compared normal serum is shown. The serum or IgG sample was added at the concentration shown to twice the volume of HeLa cell extract containing the enzyme, and pre-incubated. The final concentration in the reaction mixture was 10-fold diluted. The extracts used for each reaction were the same or prepared similarly, and the amino acid for each reaction was added in labeled form. NHS=normal human serum; Nl=normal; KS=prototype serum. *The "Relevant anti-synthetase" column shows the percent inhibition by a serum known to have autoantibodies to the synthetase for the amino acid shown, tested simultaneously. For example, results with an anti-PL-12 serum are shown in the "alanine" row, and results with an anti-EJ serum are shown in the "glycine" row. A single anti-OJ serum known to have both anti-IleRS and anti-LysRS activity was used for both the "isoleucine" and "lysine" rows.

To further demonstrate that the inhibition of AsnRS resulted from antibodies, the purified IgG fraction of KS serum was tested, at a concentration of 0.6 mg/ml in the final reaction mixture. IgG showed similar inhibition of AsnRS, by 88% at 20 minutes compared with the activity in the absence of IgG, whereas there was no significant inhibition of other synthetases (<0–16%). Normal control serum and anti-KS negative myositis serum showed no significant inhibition of AsnRS, although sera with other anti-synthetases inhibited their respective enzymes. Normal IgG inhibited only 14%.

In view of these results, sera KN and NI were similarly tested, and also showed specific inhibition of AsnRS compared to the activity with normal serum (96% and 98%, respectively). There was no significant inhibition of any of the 16 other synthetases tested (KN range <0 to 9%; NI range <0 to 27%). IgG from these sera also showed specific inhibition (87% and 64%, respectively) at a concentration of 0.3 mg/ml in the final reaction mixture.

The KS antigen was purified from HeLa cell extract by immunoaffinity chromatography using KS prototype serum. When 80-fold diluted KS antigen was tested against KS serum and NI and KN IgG by ELISA, all showed activity above controls (OD 1.19, 0.811, 1.027 respectively, vs. 0.227–0.574 for normal or other anti-synthetase sera), indicating that the affinity-purified material was active antigenically. This antigen preparation was tested for AsnRS enzymatic activity in an asparagine aminoacylation reaction and it was found to be highly active (8,059 cpm with KS antigen vs. 126 cpm without enzyme at 10 minutes), confirming that KS antigen is AsnRS.

Discussion

In the present study, a novel autoantibody was described, directed at AsnRS, the sixth in a series of autoantibodies to aminoacyl-tRNA synthetases. The evidence for its identification was similar to that provided for other anti-synthetases, including the immunoprecipitation of a distinctive set of restricted tRNAs differing from those precipitated by other anti-synthetases, a protein of a size consistent with that expected of the synthetase, and specific inhibition of the enzyme target by IgG from each patient that shows the antibody, without inhibiting other synthetases. These findings show human AsnRS to be approximately 65 kDa, similar in size to other forms of AsnRS that have been characterized (bacterial AsnRS at 53 kDa and yeast AsnRS at 51 kDa, and Brugia malayi at 63 kDa (Anselme, J., et al., Gene 84:481–485 (1989); Seignovert, L., et al., Eur. J. Biochem. 239:501–508 (1996); Kron, M., et al., FEBS Letter 374:122–124 (1995)). Recently Hartlein et al tested our prototype serum KS against a recombinant form of human AsnRS, and the serum demonstrated reactivity, providing further proof of the identification of the KS antigen as AsnRS.

Aminoacyl-tRNA synthetases are divided into Class I and Class II synthetases based on several properties shared by members of the class, including: sequence motifs (signature sequences); molecular structures (Rossman dinucleotide binding fold and parallel β-sheet regions for Class I, vs. extensive anti-parallel β-sheet regions for Class II); and the site of initial aminoacylation (Class I at the 2' OH of the terminal ribose, vs. Class II at the 3' OH of the terminal ribose) (Eriani, G., et al., Nature 347:203–206 (1990); and Cusack, S., et al., Nucleic Acids Res. 19:3489–3498 (1991)). Among higher eukaryotes, 9 synthetase activities, most of which are Class I enzymes, are associated into a multi-enzyme complex. Including AsnRS, 5 of 6 synthetase antigens are Class II aminoacyl tRNA synthetases each found free and uncomplexed in the cell cytoplasm. Anti-OJ sera immunoprecipitate the full multi-enzyme complex with 9 synthetase activities, but most anti-OJ sera react primarily with isoleucyl-tRNA synthetase, a Class I synthetase (Targoff, I. N., et al., J. Clin. Invest. 91:2556–2564 (1993)). A very small number of sera have anti-OJ by IPP but appear to be equally or more strongly reactive with lysyl-tRNA synthetase, another Class I synthetase. However, anti-OJ is one of the least common anti-synthetases, and thus, most anti-synthetase antibodies, and most anti-synthetase sera, react with uncomplexed Class II synthetases. The reason for this preference is unknown. Possibly, such antigens can be expressed on the surface or presented more easily.

Six synthetases remain that have not been found to be antigens by immunoprecipitation, and are not in the multi-enzyme complex. This, along with the fact that anti-Jo-1 is more common than all other anti-synthetases together, clearly indicates that synthetases are not randomly targeted. If antibodies to these other 6 synthetases occur, they must be extremely rare. Thousands of myositis and connective tissue disease sera, and hundreds of ILD sera, have been tested by us and others by IPP (Friedman, A. W., et al., Semin. Arthritis Rheum. 26:459–467 (1996); and Hirakata M., et al., Arthritis Rheum. 38:S321 (Abstr) (1995)). This would detect tRNAs precipitated by anti-synthetases, but unidentified antibodies that immunoprecipitate tRNA are very uncommon. However, if autoantibodies to these synthetases existed that did not immunoprecipitate tRNA, which can be seen with some animal antisera to synthetases, they may not have been detected.

All three patients with anti-KS autoantibodies had ILD, some with other associated features of connective tissue disease including Raynaud's phenomenon and arthritis, but none with any evidence of myositis or myopathy such as weakness or elevated creatine kinase. Each of the 5 previous anti-synthetases were first identified as myositis-associated autoantibodies, and then found to be associated with ILD. However, as noted above, a small number of patients may have ILD without clinical evidence of myositis, and this is more common with some anti-synthetases (anti-PL-12 and, from available evidence, anti-OJ) (Friedman, A. W., et al. Semin. Arthritis Rheum. 26:459–467 (1996)). In a recent report, none of 6 Japanese patients who had anti-PL-12 antibodies fulfilled criteria for myositis (Hirakata, =M., et al., Arthritis Rheum. 38:S321. (Abstract) (1995)). In this aspect, anti-KS appears to resemble anti-PL-12 more than anti-Jo-1. Also, like anti-PL-12, anti-KS may prove to be associated with myositis in other populations. The features that these 3 patients had can be considered to be within the spectrum of the "anti-synthetase syndrome" that has been associated with other anti-synthetases. ILD is one of the major features of the anti-synthetase syndrome, and Raynaud's phenomenon and arthritis, as seen in some anti-KS patients, are also felt to be part of the syndrome. The syndrome associated with anti-KS may be one end of the spectrum of anti-synthetase patients. This highlights the clinical importance of looking for such antibodies in patients with ILD even if no signs of myositis or of connective tissue diseases are present.

This group of autoantibodies is unique in having a combination of 3 characteristics: 1) they are directed at functionally related enzymes (performing the same function for different amino acids); 2) they are associated with a similar syndrome; and 3) they are mutually exclusive. Anti-KS antibodies seem to follow this pattern. No previously studied anti-synthetase serum has had evidence of antibodies to AsnRS, and none of the 3 anti-AsnRS sera reported here showed signs of reaction with other synthetases. The mechanism for this picture remains unknown. Several possible mechanisms have been proposed, such as similar interaction with myositis-inducing viruses (through complexes with tRNA-like structures on viral genomes (2) or anti-idiotypic mechanisms (Bunn, C. C., et al., J. Exp. Med. 163:1281–1291 (1986); and Plotz, P. H., Lancet ii:824–826 (1983)), or a similar pattern of surface expression. However, these proposed mechanisms remain speculative, and further studies could provide important clues for understanding the possible mechanisms for the development of these antibodies. Study of these antibodies may provide insight into the etiologic and pathogenetic mechanisms of myositis and ILD.

EXAMPLE 11

An ELISA-based assay for detecting anti-hsAsnRsc antibodies in serum from a patient is tested to determine whether the assay would be useful for determining whether a patient has an autoimmune disease related to arthritis and interstitial lung disease without myositis. The assay is to determine whether a kit in the standard ELISA microtiter plate format would be useful for detecting antibodies from serum which bind to hsAspRCs. The assay, which is tested with KS serum, is briefly set forth below.

A series of wells of a microtiter plate are coated with the recombinant hsAspRCs from Example 2 or 6, a series coated with bovine serum albumen, and a series coated with human IgG (Sigma Chemicals, Inc., St. Louis, Mo.) using methods well known in the art to immobilize the protein to the well. KS Serum, both neat and serially diluted from 1:5 to 1:500 in Binding Buffer (10 mM Tris pH 8.0, 500 mM NaCl, 0.1% Nonidet P-40, 1% non-fat dry milk) is dispensed into sample wells of a microtiter plate coated with recombinant hsAspnRSc protein from Example 2 or Example 6. Serum is also serially diluted as above and dispensed into wells coated with bovine serum albumen which serve as negative controls and wells coated with human IgG which serve as positive controls. The microtiter plate is incubated for approximately 30 minutes to an hour at room temperature. The unbound antibodies are removed by three successive washes with Wash Buffer (10 mM Tris pH 8.0, 10 mM NaCl, 1% non-fat dry milk). Next, alkaline phosphatase conjugated anti-human IgG (Sigma Chemicals Inc.) in Binding Buffer is added to the well. The microtiter plate is incubated from 30 minutes to an hour at room temperature. Afterwards, the unbound IgG is removed with three successive washes with Wash Buffer. Next, Reaction Buffer containing 0.4 g/l of nitro-blue tetrazolium (NBT) and 1.6 g/l of 5-bromo-4-chloro-3-indolyl phosphate (BCIP) in 0.1 M Tris pH 9.0 is added to the well and the plate incubated in the dark at room temperature for approximately 30 minutes or until the color reaction develops a dark blue precipitate in the positive control wells whereas the negative control wells do not develop a blue color. Since the KS serum contains antibodies against hsAspRCs a blue precipitate forms in the sample wells. Both BCIP and NBT are available as a kit for immunodetection from Sigma Chemicals, Inc. The assay demonstrates that serum containing antibodies against hsAspRCs are detected using the ELISA-based assay.

EXAMPLE 12

A diagnostic assay based on the dip stick device for detecting anti-hsAsnRsc antibodies in serum from a patient is tested to determine whether the assay is useful for determining whether a patient has an autoimmune disease related to arthritis and interstitial lung disease without myositis. The assay, which is tested with KS serum, is briefly set forth below.

Recombinant asparaginyl-tRNA synthetase is immobilized to the membrane support according to any one of PCT Application No. WO 88/08534 to May et al., PCT Application No. WO 91/12528 to Cole et al., PCT Application No. WO 90/15327 to Gould et al., U.S. Pat. No. 4,486,530 to David et al., and U.S. Pat. No. 4,786,589 to Rounds et al.

KS serum is applied to the device and allowed to diffuse throughout the device. Serum from a "normal" person not suffering from an autoimmune disease is applied to a second device containing hsAspRCs. The KS serum causes a reaction with the hsAspRCs because it contains antibodies against hsAspRCs which form a complex with the hsAspRCs whereas the serum from a "normal" person which does not contain anti-hsAspRCs antibodies does not cause a reaction. The reaction is detected as described in PCT Application No. WO 88/08534 to May et al., PCT Application No. WO 91/12528 to Cole et al., PCT Application No. WO 90/15327 to Gould et al., U.S. Pat. No. 4,486,530 to David et al., and U.S. Pat. No. 4,786,589 to Rounds et al.

Figure 8:
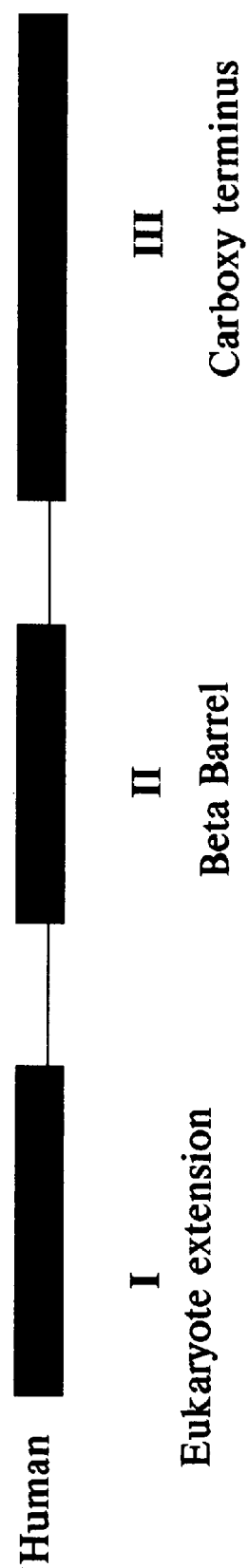
FIG. 8 is a drawing showing regions I, II and III of human AsnRS.

FIG. 8 shows the motif of human AsnRS Brugia malayi (BRUMA). Motif III is removed in order to eliminate non-specific binding of antibodies. Thus it is preferred to use the truncated protein in the kit for detecting antibodies to AsnRS.

Using site-directed mutagenesis, stop codons were introduced at residue 199. This construct, when expressed, yields a polypeptide corresponding to region I+II. Region III was NOT necessary for immunoreactivity with antiKS. Therefore, the polypeptide antigen corresponding to region I+II will be used for diagnostic assays, thus reducing non-specific antibody reactivity due to the presence of the carboxy half of the enzyme.

Based on our previous work in collaboration with EMBL-Grenoble which includes crystallization of the *Thermus thermophilus* AsnRS alone and in complex with a synthetic Asnadenylate inhibitor, synthetic asparagine-amp intermediates can be synthesized which binds specifically to the catalytic site or other biologically important regions of this family of enzymes. 5'-O-[N-(L-Asparagine)sulfamoyl] adenosine and derivatives thereof which may include hydroxamates or fluor-derivatives of the amino acid, etc, which mimic its characteristics can be shown to inhibit the asparaginyl-tRNA synthetases of one species or another, based on the species specific characteristics of each enzyme. Using this system which includes biologically active human AsnRS, one can test the specificity of new anti-microbial enzyme inhibitors, which will be useful as anti-microbial, antibacterial, anti-fungal or anti-parasitic agents. These inhibitors, testing in our recombinant enzyme assays, have potential for inhibiting the corresponding enzymes in ecto-parasites and other biological systems of human, veterinary and agricultural importance. Biologically active recombinant human and parasite AsnRS enzyme can be used to solve the three dimensional structure of these enzymes, as has been done already with the *Thermus thermophilus* bacterial enzyme. In lieu of successful crystallization of the human and parasite AsnRS, computer based homology models can be built using the known three dimensional structure of the *Thermus thermophilus* enzyme and its complex with substrates, to predict and design the synthesis of useful AsnRS enzyme inhibitors.

It is intended that the foregoing description be only illustrative of the present invention and that the present invention be limited only by the hereinafter appended claims.

What is claimed is:

1. An isolated nucleic acid sequence which encodes a human asparaginyl-tRNA synthetase having the amino acid sequence in SEQ ID NO:2.

2. The nucleic acid sequence of claim 1 wherein the nucleic acid sequence is SEQ ID NO:1.

3. The isolated nucleic acid sequence of claim 1 wherein said nucleic acid sequence is contained in *Escherichia coli* BL21 (DE3) cells as deposited under ATCC Accession No. PTA-2657.

4. An isolated nucleic acid sequence which encodes a fusion protein comprising a human asparaginyl-tRNA synthetase, which human asparaginyl-tRNA synthetase has the amino acid sequence in SEQ ID NO:2.

5. An isolated nucleic acid sequence of claim 4, wherein said nucleic acid sequence is contained in *Escherichia coli* BL21 (DE3) cells as deposited under ATCC Accession No. PTA-2657.

6. The nucleic acid sequence according to any one of claims 1, 2, 3, 4, or 5 which is essentially pure.

7. A recombinant nucleic acid vector comprising a nucleic acid sequence according to any one of claims 1, 2, 3, 4, or 5.

8. The recombinant nucleic acid vector according to claim 7 that is pCalhsAsnRSc, from *Escherichia coli* strain BL21 (DE3) deposited under ATCC Accession No. PTA-2657.

9. A host cell comprising a recombinant nucleic acid vector according to claim 7.

10. A host cell comprising a recombinant nucleic acid vector according to claim 8.

11. The recombinant host cell that is *Escherichia coli* strain BL21 (DE3) deposited under ATCC Accession No. PTA-2657.

12. A method for producing a protein which is an enzymatically active human asparaginyl-tRNA synthetase comprising:
   (a) culturing a host cell comprising a vector according to claim 7 under condition suitable for expression of said protein, and
   (b) isolating said protein.

* * * * *

SEQUENCE LISTING

```
<160> NUMBER OF SEQ ID NOS: 7

<210> SEQ ID NO: 1
<211> LENGTH: 1874
<212> TYPE: DNA
<213> ORGANISM: Homo sapiens
<300> PUBLICATION INFORMATION:
<301> AUTHORS: Beaulande, M M.
               Tarbouriech, N
               Hartlein, M
<302> TITLE: Human cytosolic asparaginyl-tRNA synthetase: cDNA
      sequence, functional expression in Escherichia coli and
      characterization as human autoantigen
<303> JOURNAL: Nucleic Acids Res.
<304> VOLUME: 26
<306> PAGES: 521-524
<307> DATE: 1998
<308> DATABASE ACCESSION NUMBER: AJ000334
<309> DATABASE ENTRY DATE: 1998-01-14

<400> SEQUENCE: 1
ccgacatgtt gagtcataag acgcgtcggt gttgcagtct gtgtccttgg aggtgaccag     60
ggccactgca ggcatggtgc tagcagagct gtacgtctct gaccgagagg gaagcgatgc    120
```

```
cacgggagat ggaaccaagg agaaaccatt taaaacaggt ctaaaggctt tgatgacagt    180
agggaaagaa ccatttccta ccatttacgt agattcacaa aaagaaaatg agaggtggaa    240
tgttatttct aaatcacagt tgaagaacat taaaaagatg tggcataggg aacaaatgaa    300
gagtgaatcc cgggaaaaga aagaggcaga agatagttta cgaagagaaa agaacctgga    360
agaagcaaag aagattacca ttaaaaatga tccaagtctc ccagagccaa aatgtgtgaa    420
gattggtgcg ttagaaggat atagaggcca aagagtaaag gtgtttggct gggtccacag    480
gctgcgcagg caaggaaaga atttaatgtt tctggtgttg cgagatggta caggttatct    540
tcagtgtgtc ttggcggatg agttgtgtca gtgctacaat ggagttctct tgtccacgga    600
gagcagtgtt gcagtgtatg gaatgctaaa tcttacccca aagggcaagc aggctccagg    660
tggccatgag ctgagttgtg acttctggga actaattggg ttggcccctg ctggaggagc    720
tgacaacctg atcaatgagg agtctgacgt tgatgtccca ctcaacaaca gacacatgat    780
gatccgagga gaaaacatgt ccaaaatcct aaaagcacga tccatggtca ccaggtgctt    840
tagagatcac ttctttgata gggggtacta tgaagttact cctccaacat tagtgcaaac    900
acaagtagaa ggtggtgcca cactcttcaa gcttgactat tttggggaag aggcattttt    960
gactcaatcc tctcagttgt acttggagac ctgcctccca gccctgggag atgtttttg    1020 tattgctcag tcataccggg cagagcagtc cagaacacga aggcacctgg ctgagtacac    1080
tcacgtggaa gctgagtgtc ctttcctgac ttttgacgac ctcctgaacc ggttggagga    1140
cttggtttgt gatgtggtag atcgaatatt gaagtcacct gcagggagca tagtgcatga    1200
gctcaacccg aactttcagc cccccaaacg gcctttcaaa cggatgaact attcagatgc    1260
tatcgtttgg ctaaaagaac atgatgtaaa gaaagaagat ggaactttct atgaatttgg    1320
agaagatatc ccagaagctc ctgagagact gatgacagac accattaatg aaccaatctt    1380
gctgtgtcga tttcctgtgg agatcaagtc cttctacatg cagcgatgtc ctgaggattc    1440
ccgtcttact gaatctgtcg acgtgttgat gcccaatgtt ggtgagattg tgggaggctc    1500
aatgcgtatc tttgatagtg aagaaatact ggcaggttat aaaagggaag ggattgaccc    1560
cactccctat tactggtata cggatcagag aaaatacggt acatgtcccc atggaggata    1620
tggcttgggc ttggaacgat tcttaacgtg gattctgaat aggtatcaca tccgagacgt    1680
gtgcttatac cctcgatttg tccagcgttg cacgccataa ccattttctc cagaagcgtg    1740
gaggaaagat tatgaaagga acaggctctt taaaaaagaa aacaaaaagc cagaatcttc    1800
ctttttttgt ttcattgggg tttctctttc tgttttttctt tctactacca taaaaactat    1860
ctcaaatcac ctga                                                     1874
```

<210> SEQ ID NO: 2
<211> LENGTH: 548
<212> TYPE: PRT
<213> ORGANISM: Homo sapiens
<300> PUBLICATION INFORMATION:
<301> AUTHORS: Beaulande, M M.
            Tarbouriech, N
            Hartlein, M
<302> TITLE: Human cytosolic asparaginyl-tRNA synthetas: cDNA
      sequence, functional expression in Escherichia coli and
      characterization as human autoantigen
<303> JOURNAL: Nucleic Acids Res.
<304> VOLUME: 26
<306> PAGES: 521-524
<307> DATE: 1998
<308> DATABASE ACCESSION NUMBER: AJ000334
<309> DATABASE ENTRY DATE: 1998-01-14

<400> SEQUENCE: 2

```
Met Val Leu Ala Glu Leu Tyr Val Ser Asp Arg Glu Gly Ser Asp Ala
 1               5                  10                  15
Thr Gly Asp Gly Thr Lys Glu Lys Pro Phe Lys Thr Gly Leu Lys Ala
                20                  25                  30
Leu Met Thr Val Gly Lys Glu Pro Phe Pro Thr Ile Tyr Val Asp Ser
            35                  40                  45
Gln Lys Glu Asn Glu Arg Trp Asn Val Ile Ser Lys Ser Gln Leu Lys
        50                  55                  60
Asn Ile Lys Lys Met Trp His Arg Glu Gln Met Lys Ser Glu Ser Arg
 65                  70                  75                  80
Glu Lys Lys Glu Ala Glu Asp Ser Leu Arg Arg Glu Lys Asn Leu Glu
                85                  90                  95
Glu Ala Lys Lys Ile Thr Ile Lys Asn Asp Pro Ser Leu Pro Glu Pro
            100                 105                 110
Lys Cys Val Lys Ile Gly Ala Leu Glu Gly Tyr Arg Gly Gln Arg Val
        115                 120                 125
Lys Val Phe Gly Trp Val His Arg Leu Arg Arg Gln Gly Lys Asn Leu
    130                 135                 140
Met Phe Leu Val Leu Arg Asp Gly Thr Gly Tyr Leu Gln Cys Val Leu
145                 150                 155                 160
Ala Asp Glu Leu Cys Gln Cys Tyr Asn Gly Val Leu Leu Ser Thr Glu
                165                 170                 175
Ser Ser Val Ala Val Tyr Gly Met Leu Asn Leu Thr Pro Lys Gly Lys
            180                 185                 190
Gln Ala Pro Gly Gly His Glu Leu Ser Cys Asp Phe Trp Glu Leu Ile
        195                 200                 205
Gly Leu Ala Pro Ala Gly Gly Ala Asp Asn Leu Ile Asn Glu Glu Ser
    210                 215                 220
Asp Val Asp Val Gln Leu Asn Asn Arg His Met Met Ile Arg Gly Glu
225                 230                 235                 240
Asn Met Ser Lys Ile Leu Lys Ala Arg Ser Met Val Thr Arg Cys Phe
                245                 250                 255
Arg Asp His Phe Phe Asp Arg Gly Tyr Tyr Glu Val Thr Pro Pro Thr
            260                 265                 270
Leu Val Gln Thr Gln Val Glu Gly Gly Ala Thr Leu Phe Lys Leu Asp
        275                 280                 285
Tyr Phe Gly Glu Glu Ala Phe Leu Thr Gln Ser Ser Gln Leu Tyr Leu
    290                 295                 300
Glu Thr Cys Leu Pro Ala Leu Gly Asp Val Phe Cys Ile Ala Gln Ser
305                 310                 315                 320
Tyr Arg Ala Glu Gln Ser Arg Thr Arg Arg His Leu Ala Glu Tyr Thr
                325                 330                 335
His Val Glu Ala Glu Cys Pro Phe Leu Thr Phe Asp Asp Leu Leu Asn
            340                 345                 350
Arg Leu Glu Asp Leu Val Cys Asp Val Val Asp Arg Ile Leu Lys Ser
        355                 360                 365
Pro Ala Gly Ser Ile Val His Glu Leu Asn Pro Asn Phe Gln Pro Pro
    370                 375                 380
Lys Arg Pro Phe Lys Arg Met Asn Tyr Ser Asp Ala Ile Val Trp Leu
385                 390                 395                 400
Lys Glu His Asp Val Lys Lys Glu Asp Gly Thr Phe Tyr Glu Phe Gly
```

-continued

Glu Asp Ile Pro Glu Ala Pro Glu Arg Leu Met Thr Asp Thr Ile Asn
            405                 410                 415
                420                 425                 430

Glu Pro Ile Leu Leu Cys Arg Phe Pro Val Glu Ile Lys Ser Phe Tyr
                435                 440                 445

Met Gln Arg Cys Pro Glu Asp Ser Arg Leu Thr Glu Ser Val Asp Val
        450                 455                 460

Leu Met Pro Asn Val Gly Glu Ile Val Gly Gly Ser Met Arg Ile Phe
465                 470                 475                 480

Asp Ser Glu Glu Ile Leu Ala Gly Tyr Lys Arg Glu Gly Ile Asp Pro
                485                 490                 495

Thr Pro Tyr Tyr Trp Tyr Thr Asp Gln Arg Lys Tyr Gly Thr Cys Pro
                500                 505                 510

His Gly Gly Tyr Gly Leu Gly Leu Glu Arg Phe Leu Thr Trp Ile Leu
            515                 520                 525

Asn Arg Tyr His Ile Arg Asp Val Cys Leu Tyr Pro Arg Phe Val Gln
        530                 535                 540

Arg Cys Thr Pro
545

<210> SEQ ID NO: 3
<211> LENGTH: 548
<212> TYPE: PRT
<213> ORGANISM: Brugia malayi
<300> PUBLICATION INFORMATION:
<308> DATABASE ACCESSION NUMBER: P10723
<309> DATABASE ENTRY DATE: 1997-11-01

<400> SEQUENCE: 3

Met Thr Val Tyr Ile Cys Pro Glu Thr Gly Asp Asp Gly Asn Asp Gly
  1               5                  10                  15

Ser Glu Leu Lys Pro Leu Arg Thr Leu Tyr Gln Ala Met Ile Ile Thr
                20                  25                  30

Lys Ser Ser Lys Gly Asp Phe Leu Ile Arg Thr Lys Lys Asp Gly Lys
            35                  40                  45

Gln Ile Trp Glu Ala Ala Ser Lys Thr Ala Leu Lys Lys Ser Trp Lys
        50                  55                  60

His Tyr Glu Gln Glu Met Leu Lys Asn Glu Lys Val Ala Ala Lys Met
 65                  70                  75                  80

Leu Glu Lys Asp Ala Thr Glu Val Gly Val Lys Ala Ala Leu Glu Glu
                85                  90                  95

Ala Lys Lys Val Gln Ile Glu Leu Asp Thr Ser Leu Ser Tyr Ile Thr
            100                 105                 110

Gly Val Lys Ile Arg Asp Leu Val Lys His Arg Asn Glu Arg Val Cys
        115                 120                 125

Ile Lys Gly Trp Ile His Arg Met Arg Arg Gln Gly Lys Ser Leu Met
    130                 135                 140

Phe Phe Ile Leu Arg Asp Gly Thr Gly Phe Leu Gln Val Leu Leu Met
145                 150                 155                 160

Asp Lys Leu Cys Gln Thr Tyr Asp Ala Leu Thr Val Asn Thr Glu Cys
                165                 170                 175

Thr Val Glu Ile Tyr Gly Ala Ile Lys Glu Val Pro Glu Gly Lys Glu
            180                 185                 190

Ala Pro Asn Gly His Glu Leu Ile Ala Asp Phe Trp Lys Ile Ile Gly
        195                 200                 205

```
Asn Ala Pro Pro Gly Gly Ile Asp Asn Val Leu Asn Glu Glu Ala Ser
    210                 215                 220
Val Asp Lys Met Leu Asp Asn Arg His Leu Val Ile Arg Gly Glu Asn
225                 230                 235                 240
Ala Ala Ala Leu Leu Arg Leu Arg Ala Ala Thr Arg Ala Met Arg
                245                 250                 255
Glu His Phe Tyr Asn Ala Gly Tyr Leu Glu Val Ala Pro Pro Thr Leu
            260                 265                 270
Val Gln Thr Gln Val Glu Gly Gly Ser Thr Leu Phe Asn Leu Asp Tyr
        275                 280                 285
Phe Gly Glu Gln Ser Phe Leu Thr Gln Ser Ser Gln Leu Tyr Leu Glu
    290                 295                 300
Thr Cys Ile Pro Thr Leu Gly Asp Val Phe Leu His Cys Ser Val Leu
305                 310                 315                 320
Gln Gly Gly Lys Ile Ser His Ser Ser Thr Leu Ala Glu Tyr Ala His
                325                 330                 335
Val Glu Ala Glu Cys Pro Phe Ile Thr Leu Asp Asp Leu Met Glu Lys
            340                 345                 350
Ile Glu Glu Leu Val Cys Asp Thr Val Asp Arg Leu Leu Ala Asp Glu
        355                 360                 365
Glu Ala Lys Lys Leu Leu Glu His Ile Asn Pro Lys Phe Gln Pro Pro
    370                 375                 380
Glu Arg Pro Phe Leu Arg Met Glu Tyr Lys Asp Ala Ile Lys Trp Leu
385                 390                 395                 400
Gln Glu His Asn Val Glu Asn Glu Phe Gly Asn Thr Phe Thr Tyr Gly
                405                 410                 415
Glu Asp Ile Ala Glu Ala Ala Glu Arg Phe Met Thr Asp Thr Ile Asn
            420                 425                 430
Lys Pro Ile Leu Leu Asn Arg Phe Pro Ser Glu Ile Lys Ala Phe Tyr
        435                 440                 445
Met Gln Arg Asp Ala Gln Asp Asn Thr Leu Thr Glu Ser Val Asp Leu
    450                 455                 460
Leu Met Pro Gly Val Gly Glu Ile Val Gly Gly Ser Met Arg Ile Trp
465                 470                 475                 480
Lys Phe Asp Glu Leu Ser Lys Ala Phe Lys Asn Val Glu Ile Asp Pro
                485                 490                 495
Lys Pro Tyr Tyr Trp Tyr Leu Asp Gln Arg Leu Tyr Gly Thr Cys Pro
            500                 505                 510
His Gly Gly Tyr Gly Leu Gly Leu Glu Arg Phe Ile Cys Trp Leu Thr
        515                 520                 525
Asn Thr Asn His Ile Arg Asp Val Cys Leu Tyr Pro Arg Phe Val Gly
    530                 535                 540
Arg Cys Val Pro
545

<210> SEQ ID NO: 4
<211> LENGTH: 554
<212> TYPE: PRT
<213> ORGANISM: Saccharomyces cerevisiae
<300> PUBLICATION INFORMATION:
<308> DATABASE ACCESSION NUMBER: P38707
<309> DATABASE ENTRY DATE: 1998-07-15

<400> SEQUENCE: 4

Met Ser Ser Leu Tyr Ile Lys Glu Ala Thr Gly Val Asp Glu Leu Thr
  1               5                  10                  15
```

-continued

```
Thr Ala Gly Ser Gln Asp His Pro Phe Lys Thr Pro Ala Tyr Ala Leu
            20                  25                  30

Phe Ala Ser Gln Gln Lys Ser Asp Ala Thr Glu Pro Lys Leu Phe Val
        35                  40                  45

Phe Lys Thr Glu Asp Asn Glu Tyr Gln Glu Ile Ser Ala Ser Ala Leu
    50                  55                  60

Lys Lys Ala Arg Lys Gly Cys Asp Gly Leu Lys Lys Ala Val Lys
65                  70                  75                  80

Gln Lys Glu Gln Glu Leu Lys Lys Gln Lys Glu Ala Glu Asn Ala
            85                  90                  95

Ala Lys Gln Leu Ser Ala Leu Asn Ile Thr Ile Lys Glu Asp Glu Ser
        100                 105                 110

Leu Pro Ala Ala Ile Lys Thr Arg Ile Tyr Asp Ser Tyr Ser Lys Val
    115                 120                 125

Gly Gln Arg Val Lys Val Ser Gly Trp Ile His Arg Leu Arg Ser Asn
        130                 135                 140

Lys Lys Val Ile Phe Val Val Leu Arg Asp Gly Ser Gly Phe Ile Gln
145                 150                 155                 160

Cys Val Leu Ser Gly Asp Leu Ala Leu Ala Gln Gln Thr Leu Asp Leu
            165                 170                 175

Thr Leu Glu Ser Thr Val Thr Leu Tyr Gly Thr Ile Val Lys Leu Pro
        180                 185                 190

Glu Gly Lys Thr Ala Pro Gly Gly Val Glu Leu Asn Val Asp Tyr Tyr
    195                 200                 205

Glu Val Val Gly Leu Ala Pro Gly Gly Glu Asp Ser Phe Thr Asn Lys
    210                 215                 220

Ile Ala Glu Gly Ser Asp Pro Ser Leu Leu Asp Gln Arg His Leu
225                 230                 235                 240

Ala Leu Arg Gly Asp Ala Leu Ser Ala Val Met Lys Val Arg Ala Ala
            245                 250                 255

Leu Leu Lys Ser Val Arg Arg Val Tyr Asp Glu Glu His Leu Thr Glu
        260                 265                 270

Val Thr Pro Pro Cys Met Val Gln Thr Gln Val Glu Gly Gly Ser Thr
    275                 280                 285

Leu Phe Lys Met Asn Tyr Tyr Gly Glu Glu Ala Tyr Leu Thr Gln Ser
    290                 295                 300

Ser Gln Leu Tyr Leu Glu Thr Cys Leu Ala Ser Leu Gly Asp Val Tyr
305                 310                 315                 320

Thr Ile Gln Glu Ser Phe Arg Ala Glu Lys Ser His Thr Arg Arg His
            325                 330                 335

Leu Ser Glu Tyr Thr His Ile Glu Ala Glu Leu Ala Phe Leu Thr Phe
        340                 345                 350

Asp Asp Leu Leu Gln His Ile Glu Thr Leu Ile Val Lys Ser Val Gln
    355                 360                 365

Tyr Val Leu Glu Asp Pro Ile Ala Gly Pro Leu Val Lys Gln Leu Asn
    370                 375                 380

Pro Asn Phe Lys Ala Pro Lys Ala Pro Phe Met Arg Leu Gln Tyr Lys
385                 390                 395                 400

Asp Ala Ile Thr Trp Leu Asn Glu His Asp Ile Lys Asn Glu Glu Gly
            405                 410                 415

Glu Asp Phe Lys Phe Gly Asp Asp Ile Ala Glu Ala Ala Glu Arg Lys
        420                 425                 430
```

```
Met Thr Asp Thr Ile Gly Val Pro Ile Phe Leu Thr Arg Phe Pro Val
        435                 440                 445

Glu Ile Lys Ser Phe Tyr Met Lys Arg Cys Ser Asp Asp Pro Arg Val
        450                 455                 460

Thr Glu Ser Val Asp Val Leu Met Pro Asn Val Gly Glu Ile Thr Gly
465                 470                 475                 480

Gly Ser Met Arg Ile Asp Asp Met Asp Glu Leu Met Ala Gly Phe Lys
                    485                 490                 495

Arg Glu Gly Ile Asp Thr Asp Ala Tyr Tyr Trp Phe Ile Asp Gln Arg
                500                 505                 510

Lys Tyr Gly Thr Cys Pro His Gly Gly Tyr Gly Ile Gly Thr Glu Arg
                515                 520                 525

Ile Leu Ala Trp Leu Cys Asp Arg Phe Thr Val Arg Asp Cys Ser Leu
        530                 535                 540

Tyr Pro Arg Phe Ser Gly Arg Cys Lys Pro
545                 550
```

<210> SEQ ID NO: 5
<211> LENGTH: 438
<212> TYPE: PRT
<213> ORGANISM: Thermus aquaticus
<300> PUBLICATION INFORMATION:
<308> DATABASE ACCESSION NUMBER: X91009
<309> DATABASE ENTRY DATE: 1996-08-21

<400> SEQUENCE: 5

```
Met Arg Val Phe Ile Asp Glu Ile Ala Arg His Val Asp Gln Glu Val
  1               5                  10                  15

Glu Leu Arg Gly Trp Leu Tyr Gln Arg Arg Ser Lys Gly Lys Ile His
            20                  25                  30

Phe Leu Ile Leu Arg Asp Gly Thr Gly Phe Leu Gln Ala Thr Val Val
        35                  40                  45

Gln Gly Glu Val Pro Glu Ala Val Phe Arg Glu Ala Asp His Leu Pro
 50                  55                  60

Gln Glu Thr Ala Leu Arg Val Trp Gly Arg Val Arg Glu Asp Arg Arg
 65                  70                  75                  80

Ala Pro Gly Gly Phe Glu Leu Ala Val Arg Asp Leu Gln Val Val Ser
                 85                  90                  95

Arg Pro Gln Gly Glu Tyr Pro Ile Gly Pro Lys Glu His Gly Ile Asp
            100                 105                 110

Phe Leu Met Asp His Arg His Leu Trp Leu Arg His Arg Arg Pro Phe
        115                 120                 125

Ala Val Met Arg Ile Arg Asp Glu Leu Glu Arg Ala Ile His Glu Phe
    130                 135                 140

Phe Gly Glu Arg Gly Phe Leu Arg Phe Asp Ala Pro Ile Leu Thr Pro
145                 150                 155                 160

Ser Ala Val Glu Gly Thr Thr Glu Leu Phe Glu Val Glu Leu Phe Asp
                165                 170                 175

Gly Glu Lys Ala Tyr Leu Ser Gln Ser Gly Gln Leu Tyr Ala Glu Ala
            180                 185                 190

Gly Ala Leu Ala Phe Ala Lys Val Tyr Thr Phe Gly Pro Thr Phe Arg
        195                 200                 205

Ala Glu Arg Ser Lys Thr Arg Arg His Leu Leu Glu Phe Trp Met Val
    210                 215                 220

Glu Pro Glu Val Ala Phe Met Thr His Glu Glu Asn Met Ala Leu Gln
225                 230                 235                 240
```

-continued

```
Glu Glu Leu Val Ser Phe Leu Val Ala Arg Val Leu Glu Arg Arg Ser
                245                 250                 255
Arg Glu Leu Glu Met Leu Gly Arg Asp Pro Lys Ala Leu Glu Pro Ala
            260                 265                 270
Ala Glu Gly His Tyr Pro Arg Leu Thr Tyr Lys Glu Ala Val Ala Leu
        275                 280                 285
Val Asn Arg Ile Ala Gln Glu Asp Pro Glu Val Pro Pro Leu Pro Tyr
    290                 295                 300
Gly Glu Asp Phe Gly Ala Pro His Glu Ala Ala Leu Ser Arg Arg Phe
305                 310                 315                 320
Asp Arg Pro Val Phe Val Glu Arg Tyr Pro Ala Arg Ile Lys Ala Phe
                325                 330                 335
Tyr Met Glu Pro Asp Pro Glu Asp Pro Glu Leu Val Leu Asn Asp Asp
            340                 345                 350
Leu Leu Arg Pro Glu Gly Tyr Gly Glu Ile Ile Gly Gly Ser Gln Arg
        355                 360                 365
Ile His Asp Leu Glu Leu Leu Arg Arg Lys Ile Gln Glu Phe Gly Leu
    370                 375                 380
Pro Glu Glu Val Tyr Asp Trp Tyr Leu Asp Leu Arg Arg Phe Gly Ser
385                 390                 395                 400
Val Pro His Ser Gly Phe Gly Leu Gly Leu Glu Arg Thr Val Ala Trp
                405                 410                 415
Ile Cys Gly Leu Ala His Val Arg Glu Ala Ile Pro Phe Pro Arg Met
            420                 425                 430
Tyr Thr Arg Met Arg Pro
            435
```

<210> SEQ ID NO: 6
<211> LENGTH: 30
<212> TYPE: DNA
<213> ORGANISM: Artificial Sequence
<220> FEATURE:
<223> OTHER INFORMATION: Description of Artificial Sequence: primer
      complementary to SEQ ID NO: 1

<400> SEQUENCE: 6
ccggatccca tatggtgcta gcagagctgt                                    30

<210> SEQ ID NO: 7
<211> LENGTH: 27
<212> TYPE: DNA
<213> ORGANISM: Artificial Sequence
<220> FEATURE:
<223> OTHER INFORMATION: Description of Artificial Sequence: 3' primer
      complementary to SEQ ID NO: 1

<400> SEQUENCE: 7
tcaggtgatt tgagatagtt tttatgg                                       27